(12) United States Patent
Fabis

(10) Patent No.: US 12,403,461 B2
(45) Date of Patent: Sep. 2, 2025

(54) SOLID-PHASE CHELATOR MATERIAL, METHOD FOR PRODUCING THEREOF AND USE THEREOF FOR THE PURIFICATION OF PROTEINS

(71) Applicant: Cube Biotech GmbH, Monheim (DE)

(72) Inventor: Roland Fabis, Leverkusen (DE)

(73) Assignee: CUBE BIOTECH GMBH, Monheim (DE)

( * ) Notice: Subject to any disclaimer, the term of this patent is extended or adjusted under 35 U.S.C. 154(b) by 352 days.

(21) Appl. No.: 17/296,928

(22) PCT Filed: Nov. 22, 2019

(86) PCT No.: PCT/EP2019/082224
§ 371 (c)(1),
(2) Date: May 25, 2021

(87) PCT Pub. No.: WO2020/109162
PCT Pub. Date: Jun. 4, 2020

(65) Prior Publication Data
US 2022/0023851 A1    Jan. 27, 2022

Related U.S. Application Data

(60) Provisional application No. 62/772,206, filed on Nov. 28, 2018.

(51) Int. Cl.
B01J 45/00    (2006.01)
B01D 15/38    (2006.01)
(Continued)

(52) U.S. Cl.
CPC .......... *B01J 45/00* (2013.01); *B01D 15/3828* (2013.01); *B01J 20/3208* (2013.01);
(Continued)

(58) Field of Classification Search
None
See application file for complete search history.

(56) References Cited

FOREIGN PATENT DOCUMENTS

WO    2006013042 A2    2/2006
WO    2017046625 A1    3/2017

OTHER PUBLICATIONS

Macrocyclics.com, "Safety Data Sheet for 1,4,7,10-tetraazacyclododecane." Published Jul. 6, 2016; viewed on Dec. 23, 2024 at https://macrocyclics.com/wp-content/uploads/2018/02/M-100-6.pdf.*

(Continued)

*Primary Examiner* — Daniel Berns
(74) *Attorney, Agent, or Firm* — Biotech Beach Law PC; Raymond Wagenknecht

(57) ABSTRACT

A solid-phase chelator material usable for the purification of proteins. The solid-phase chelator material comprises a solid phase, polyamine groups bound to the solid phase and chelating groups bound to the polyamine groups. At least a part of the polyamine groups is connected with at least two chelating groups per polyamine group. Each chelating group comprises one or several aminopolycarboxylic acid groups (APA groups), with the proviso that the number of APA groups per polyamine group connected with at least two cheating groups is at least three.

19 Claims, 3 Drawing Sheets

(51) Int. Cl.
    *B01J 20/28*          (2006.01)
    *B01J 20/32*          (2006.01)
    *C07K 1/22*           (2006.01)

(52) U.S. Cl.
    CPC ....... *B01J 20/3219* (2013.01); *B01J 20/3265* (2013.01); *C07K 1/22* (2013.01)

(56) References Cited

OTHER PUBLICATIONS

PCT/EP2019/08224 International Search Report mailed Mar. 10, 2020.

\* cited by examiner

SOLID-PHASE CHELATOR MATERIAL, METHOD FOR PRODUCING THEREOF AND USE THEREOF FOR THE PURIFICATION OF PROTEINS

CROSS REFERENCE TO RELATED APPLICATIONS

This is a US national phase entry under 35 U.S.C. § 371 of international patent application no. PCT/EP2019/082224, filed 22 Nov. 2019, which claims priority to U.S. provisional patent application No. 62/772,206, filed 28 Nov. 2018; the entire content of each is herein incorporated by reference in its entirety.

TECHNICAL FIELD

The present invention relates to the field of solid-phase chelator materials and methods for producing such solid-phase chelator materials. Furthermore, the invention relates to a method for purifying polypeptides and proteins with a metal-loaded solid-phase chelator material and the use of a metal-loaded solid-phase chelator material inter alia for the immobilized metal affinity purification of proteins.

BACKGROUND

Immobilized metal affinity chromatography (IMAC), developed by Porath (Nature 258:598, 1975), has been implemented as a standard method for purification of recombinant proteins, and is still one of the favored methods, when high quantities of recombinant proteins have to be purified.

The principle of this method is basing upon the introduction of a plurality of histidine groups to the amino acid side chain of the proteins, which gives them a higher affinity towards immobilized metal ions. These so-called "his-tags" consist of consecutive histidine residues, as well as histidine, combined with other amino acids, and usually six to ten histidines. These "his-tags" show a much higher affinity to immobilized metal ions than natural proteins, so that a high degree of purification is possible, especially, when some small concentrations of imidazole are added to the binding and washing buffer, which reduces non-specific interactions of proteins without his-tag.

Alternatively, IMAC can be used for the purification of phosphoproteins, where the metal ion directly binds to phosphate groups. With this method, phosphoproteins can be separated from proteins without phosphate groups, which show no or almost weak binding to metal ions.

Combined with metals, such as Zn and Cu, IMAC resins can be used for reversibly binding metal-conjugating proteins, such as zinc finger proteins and copper-interacting proteins like cupredoxin or hemocyanin.

The ligands, used for IMAC, can be classified by the number of coordinating positions, which the ligand can occupy on the metal ion. So, chelators are called tridentate, when they obtain three metal ion-binding groups, such as amine, carboxy, phosphate, and the like. Tetradentate chelators can coordinate onto four positions on the metal ion, and pentadentate chelators can occupy five positions.

Since more than twenty years, solid-phase immobilized iminodiacetic acid (IDA), which is a tridentate chelator, and nitrilotriacetic acid (NTA), a tetradentate chelator, are established as standard materials for IMAC. Alternative chelators, which are also commercially available, are the tetradentate "Talon" ligand, as well as pentadentate chelators, such as tris-carboxymethyl ethylene diamine (TED). In the last years, some pentadentate chelator-based resins, such as cOmplete His Tag Resin (Roche Diagnostics GmbH) and Ni Sepharose Excel (GE Healthcare) have entered the market.

For IMAC, the application of many different metals has been successfully performed, so for instance Ni, Co, Cu, Fe, Ca, Zn, Al, Eu, Ga, Sc have been investigated. For the purification of phosphoproteins, Al in combination with IDA, as well as Fe, Ga and Eu in combination with NTA, are widely used.

It should be noted that especially iminodiacetic acid which can be obtained very easily and with low costs, has the disadvantage, that metal ions are fixed to the solid phase with only three functionalizations and so it is known, that metal ions are leached into the buffers, so that the protein binding capacity is reduced and the elution buffer can contain small traces of metal ions. And, with almost three free coordination sites for this-protein at the metal ion some proteins without his-tag are also bound to the resin, so that after purification contaminated eluates are obtained.

Tetradentate chelators, such as NTA, are much more stable in terms of metal leaching, but loose metal ions during purification, when other chelators, such as EDTA, or reductants, such as DTT, are present in the lysis buffer. EDTA, as a stronger chelator, which removes membrane-stabilizing magnesium ions and is necessary for inhibiting metalloproteases in lysis buffer, removes almost all the metal ions from NTA resin, when its concentration is higher than 2 mM. Addition of DTT (dithiothreitol), which helps stabilizing the protein SH groups against oxidation to disulfides and protein dimerization, reduces metal ions, such as nickel, to the uncharged metal, so that the protein binding affinity is significantly lowered.

These drawbacks can be reduced by using stable pentavalent chelators, which strongly bind the metal ion, so that it cannot be removed by EDTA containing buffers. In addition to that, complexes of e.g. nickel with a pentadentate chelator are remarkably stable against reductants, such as DTT.

Metal affinity chromatography for purifying recombinant his-tagged proteins was introduced by Porath et al. (Nature 258, 598-599, 1975). This new technology uses the discovery, that metal ions, such as $Cu^{2+}$ and $Zn^{2+}$, bound to a solid phase via a chelator, interact with donor groups of histidine amino acids of protein side chains. This interaction is effective at a higher pH value, where the histidines remain non-protonated, while at lower pH values, where the histidines are protonated, the proteins can be eluted from the metal ion-modified solid phase. The ligand used for immobilization of metal ions is iminodiacetic acid, but, in case of using nickel as metal, IDA binds nickel with three coordinating groups, so that the stability of the nickel-chelator complex is too low against pH changes, chelating agents and reduction agents in solution, and metal leaching from the surface is observed.

EP 0 253 303 A2 by Hochuli et al. relates to a tetradentate ligand, basing on a substituted nitrilotriacetic acid, which is prepared by carboxymethylation of z-ε-lysine, deprotection, coupling onto epoxy-activated agarose and charging with nickel. With this material, an improvement compared to iminodiacetic acid can be achieved, that metal leaching is drastically reduced, while the stability against chelators, such as EDTA, and reducing agents remains limited.

In EP 1 276 716 Kappel et al. describe a thioether-bound NTA ligand. The limitations are the same as with amino-coupled nitrilotriacetic acid.

In U.S. Pat. No. 6,441,146 Minh describes the synthesis of a pentavalent chelator resin by epoxyfunctionalization, coupling of lysine while blocking the α nitrogen and subsequent carboxymethylation. This substance can be used as material for covalent immobilization by use of e.g. carbodiimide chemistry.

In Talanta 1989, 36, 341-346 McCurley et al. developed an IMAC resin, based on immobilized tris(carboxymethyl) ethylene diamine (TED) by coupling ethylene diamine and carboxymethylation of the product. But according to the evidence of the article, only a mixture of TED and ethylenediamine-N,N'-diacetic acid could be obtained.

Haner et al. use a cobalt-pentadentate chelator for the removal of calcium ions, synthesized by activation of EDTA by carbodiimide chemistry and coupling onto amine-functionalized agarose.

In EP 2 022 561 by Goerlich et al. describe a method for binding a polycarboxylic acid, such as EDTA or DTPA, to an amine-modified solid phase in presence of an excess of a condensing agent, e.g. 1-Ethyl-3-(3-dimethylaminopropyl) carbodiimide (EDC), is presented. In addition to that, a coupling onto the polycarboxylate via only one carboxy group is claimed.

A chelator with at least six coordination groups is described in EP 2 183 049 by Goerlich et al. The chelator is immobilized by means of a carboxamide bond through one single carboxy group, for immobilized metal affinity chromatography (IMAC) in the purification of recombinant proteins with a plurality of histidine residues.

In WO 2009/008802 Andersson et al. describe the synthesis of a pentadentate chelator via coupling a carboxylic acid anhydride to an amide-functionalized agarose via acid anhydride, so that the product is suitable for detection and purification of recombinant proteins.

There are some examples for coupling EDTA and DTPA onto bifunctional linkers. In U.S. Pat. No. 5,281,704, example 6, a chemical compound, consisting of two DTPA molecules, linked via amide bonds, is prepared by coupling DTPA tetramethyl ester with ethylene diamine after activation with dicyclohexyl carbodiimide, and subsequent hydrolysis in sodium hydroxide solution. In addition to that, other chelators, like DOTA, EDTA, and TTHA are mentioned as part of linker-connected dimeric chelators, with a connection to the linker via ester- or amide functions.

In Reactive and Functional Polymers, 29 (1996) 29-39, Brosse et al. coupled EDTA- and DTPA anhydride with ethylene glycol, N-methyl diethanolamine, ethylene diamine, and many other diols and diamines. Tuelue and Geckeler prepared polycondensates of EDTA and DTPA with polyethylene glycols by a one-step reaction of the chelator anhydrides with diols.

In Macromol. Rapid Commun. 2001, 22, 855±858, by Geckeler et al. the synthesis of a water soluble sugar copolymer, with pendant carboxy groups, that was biodegradable and metal complexing, is published. But linker-connected chelators, immobilized to a solid phase via only one carboxylic acid, forming solid-phase bound chelator chains, are not published until now.

In US 2013/0072638 by Algotsson et al. a dimeric pentadentate chelator is prepared which gives a strong binding of metal ions, connected via a scaffold and coupled to carbohydrate material by a group, which is connected to the scaffold. Here dimeric chelators offer a cooperative binding effect due to the binding of two adjacent immobilized metal ions, which leads to a stronger binding of proteins, compared to a monomeric pentavalent chelator. But due to the steric demand of the branched linker with two chelator functions, the material according to that invention only has a limited chelating group density and thus protein binding capacity.

WO 2017/046625 A1 describes a synthesis of a chelator with chelator chains which has a high binding capacity for his-tagged proteins.

It is an object of the present invention to provide an improved solid-phase chelator material having improved properties which is inter alia usable for the affinity purification of recombinant proteins, especially when the chelator material is metal loaded.

SUMMARY OF THE INVENTION

In one aspect of the invention a solid-phase chelator material is provided, which includes a solid phase, polyamine groups bound to the solid phase and chelating groups bound to the polyamine groups, wherein at least a part of the polyamine groups are connected with at least two chelating groups per polyamine group and wherein each chelating group comprises one or several aminopolycarboxylic acid groups (APA groups), with the proviso that the number of APA groups per polyamine group connected with at least two chelating groups is at least three.

In some embodiments the chelating groups are selected from the group consisting of individual APA groups, linear chelator chains formed by two or more APA groups which are connected with each other via bifunctional linker moieties K, branched chelator chains formed by three or more APA groups connected with each other via trifunctional linker moieties L, and mixed chelator chains formed by four or more APA groups connected with each other via at least one bifunctional linker moiety K and at least one trifunctional linker moiety L.

In some embodiments the number of chelating groups bound to a polyamine group is at least three, preferably at least four, and/or wherein the number of APAs which is coupled to a polyamine group connected with at least two chelating groups is in the range from 3 to 20, preferably in the range from 4 to 15.

In some embodiments, the polyamine groups are derived from the polyamines which are selected from the group consisting of diethylene triamine, triethylene tetramine, tetraethylene pentamine, pentaethylene hexamine, linear and branched polyethylene imine, poly-lysine, polypropylene imine, macrocylic polyamines like cyclam, cyclen, and 1,4,7-triazacyclononane, branched polyamines like 1,1,1-tris(aminomethyl)ethane, tris-aminoethyl amine, tris aminopropyl amine, tetrakis-ethylamino amine, tetrakis-ethylamino amine, tetrakis-aminopropyl amine, and amine functionalized tetrafunctional branched PEGs, basing on a pentaerithritol core, preferably selected from the group consisting of diethylene triamine, triethylene tetramine, tetraethylene pentamine and pentaethylene hexamine, more preferably selected from the group consisting of triethylene tetramine, tetraethylene pentamine and pentaethylene hexamine.

In some embodiments, the APA groups are derived from the APAs which are selected from the group consisting of ethylenediaminetetraacetic acid, diethylenetriaminepentaacetic acid, triethylenetetraminehexaacetic acid, ethylenediamine-N,N'-disuccinic acid, ethyleneglycol-bis(β-aminoethyl ether)-N,N,N',N'-tetraacetic acid, 1,4,7,10-tetraazacyclododecane-1,4,7,10-tetraacetic acid, and 1,4,7-triazacyclononane-1,4,7-trisacetic acid.

In some embodiments, at least a part or all of the chelating groups have the general formula -(APA1-K$_n$-APA2 in which APA1 and APA2 are identical or different from each other, n is an integer in the range from 1 to 50 and K is a bifunctional linker moiety.

In some embodiments, at least a part or all of the chelating groups

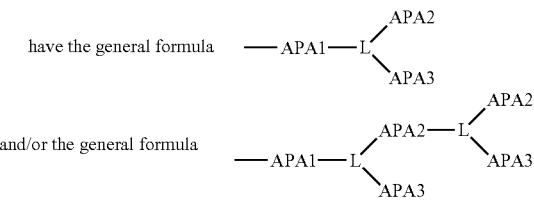

in which APA1, APA2 and APA3 are aminopolycarboxylic acid groups which are identical or different from each other and L is a trifunctional linker moiety.

In some embodiments, the APAs and the linker moieties and/or the chelating groups and the polyamine groups are connected with each other via an amide moiety.

In some embodiments the bifunctional linker moiety K is selected from the group consisting of A-$(CH_2)_n$—B, A-Q-B and A-$(C_2H_4O)_m$—$(CH_2)_o$—B, in which A and B are functional groups which are able react with carboxy groups, namely OH, $NH_2$, NHR, Cl, Br, I, OMs, OTs, $N_3$, wherein R is a hydrocarbon group with the formula $C_nH_{2n+1}$, in which n is an integer in the range from 1 to 6, m is an integer in the range from 1 to 12, o is an integer in the range from 2 to 12, Q is a straight or branched configuration of 2 to 100 atoms, optionally containing C, H, N, O and S, including cyclic compounds, such as carbohydrates, preferably a diamine $NH_2$ or NHR which is more preferably selected from the group consisting of ethylenediamine, 1,4-diaminobutane, 1,6-diaminohexane, 1,8-diaminooctane, and Jeffamine ED600; and the trifunctional linker moiety L has one of the general formulas

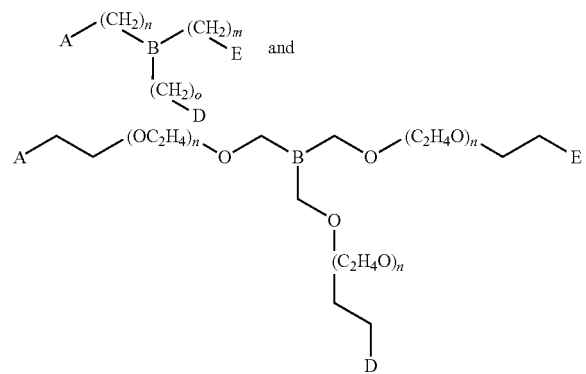

in which A, D and E are functional groups which are able to react with a carboxy group, preferably —$NH_2$ or —NHR, B is a branching atom, preferably C or N, which is connected with at least three stable bonds preferably to carbon atoms, connected with functional groups, n, m and o are integers in the range from 2 to 30; and is preferably a triamine, which is more preferably selected from the group consisting of diethylene triamine, tris(2-aminoethyl)amine, tris(2-aminopropyl)amine and amino-functionalized trifunctional branched PEGs based on a glycerol core.

In some embodiments a spacer moiety is inserted between the solid phase and the polyamine groups which is preferably derived from the group consisting of epichlorohydrine, epibromohydrine, 1,2-ethylene glycol diglycidyl ether, 1,4-butanediol diglycidyl ether, allyl glycidyl ether and allyl bromide.

In some embodiments, the solid phase is selected from the group consisting of agarose, cellulose, agar, dextran, chitosan, alginate, gellan, preferably agarose; and/or silica, titanium dioxide, zirconium dioxide, aluminum dioxide, other metal- or semi-metal-oxides, gold, glass; and/or acrylates, methacrylates, acrylamides, styrene derivatives, vinyl esters, vinyl amides, and vinyl alcohol; and/or porous chromatographic supports, non-porous chromatographic supports, membranes, coated surfaces, coated tubes, sensor surfaces, microarray surfaces, coated microtiter plates; and/or magnetic agarose, magnetic silica and a magnetic polymer, preferably magnetic agarose; and/or dextran modified gold chips, magnetic beads.

Also provides is a metal ion loaded solid-phase chelator material comprising a solid-phase chelator material as described that is loaded with metal ions selected from the group consisting of $Ni^{2+}$, $Co^{2+}$, $Cu^{2+}$, $Zn^{2+}$, $Al^{3+}$, $Fe^{3+}$, $Eu^{3+}$, $Ga^{3+}$, $Mn^{2+}$, and $Ca^{2+}$.

Also provided is a method for producing a solid-phase chelator material as described, which includes covalently binding at least three monomeric APAs on a solid phase having polyamine groups bound thereto under formation of polyamine groups having at least three monomeric APA groups bound thereto via an amide group; or covalently binding at least two APAs on a solid phase having polyamine groups bound thereto under formation of a solid-phase material with polyamine groups having at least two APA groups bound thereto via an amide group, adding a bifunctional linker K or a trifunctional linker L to said solid-phase material, reacting said coupled linker with a carboxy group of a second APA, thereby forming a solid-phase chelator material having linear chelator chains or branched chelator chains of APA groups bound to the polyamine groups bound to the solid phase, optionally repeating the steps of adding a linker and then adding a further APA for extending the length of the linear chelator chains or the branched chelator chains; or reacting at least two monomeric APAs with a bifunctional linker K or at least three monomeric APAs with a trifunctional linker L under formation of a multimeric APA chelator comprising a linear chelator chain or a branched chelator chain and covalently binding at least two multimeric APA chelators on a solid phase having polyamine groups bound thereto under formation of polyamine groups having at least two linear and/or branched chelator chains bound thereto via an amide group.

Also provided is a method for producing a solid-phase chelator material having linear chelating groups with APA groups connected via a bifunctional linker as disclosed, comprising the following steps: a) providing an APA and a solid phase having polyamine groups bound thereto; b) coupling the APA with the solid phase in the presence of a condensing agent, wherein a single carboxy group of the APA reacts with the solid phase under binding of the APA to the solid phase; c) mixing the solid-phase material obtained in step b) with a bifunctional linker K; d) coupling the bifunctional linker K with an APA carboxy group in the presence of a condensing agent, wherein a single reactive group of the bifunctional linker K reacts with the bound APA; e) mixing the solid-phase material obtained in step d) with a further APA; f) coupling the further APA with the bifunctional linker in the presence of a condensing agent, wherein a single carboxy group of the further APA reacts with a further reactive group of the bifunctional linker K bound to the solid-phase material; g) optionally repeating step c) to f) at least one time.

Also provided is a method for producing a solid-phase chelator material having linear chelating groups with APA groups connected via a bifunctional linker as described, comprising the following steps: a) providing an APA dianhydride and a solid-phase material having polyamine groups bound thereto; b) coupling said APA dianhydride with said solid-phase material via an amino group of bound polyamine, wherein a single anhydride group per APA dianhydride reacts with an amino moiety and the other anhydride group remains unchanged; c) washing the solid-phase material obtained in step b) with an anhydrous solvent in order to remove the non-coupled dianhydride; d) providing the solid-phase material obtained in step c) and a bifunctional linker K; e) coupling the bifunctional linker K with the APA anhydride group, wherein a single amine group of the bifunctional linker K reacts with the APA anhydride group and the other functional group of the bifunctional linker K remains unchanged; f) washing the solid phase with an anhydrous solvent in order to remove the non-coupled linker molecules; g) providing the solid-phase material obtained in step f) and additional APA dianhydride; h) coupling said APA dianhydride to said bifunctional linker K, wherein a single carboxy group per APA reacts with the remaining functional group of the bifunctional linker K; l) optionally repeating step c) to h) at least one time.

Also disclosed is a method for producing a solid-phase chelator material having linear chelating groups with APA groups connected via a bifunctional linker as described, comprising the following steps: a) providing an APA dianhydride and a bifunctional linker K in a ratio of 2:1 to 1:1, preferably 2:1 to 1.25:1; b) coupling the APA dianhydride to said bifunctional linker K via an amine or a hydroxy group on the linker, wherein the linker reacts with two different dianhydrides, so that a substance APA1-K-(APA2-K)$_n$-APA3 is formed, wherein APA1 is an APA with one anhydride group and one amide function, APA2 is an APA with two amide functions, and APA3 is an APA with one anhydride group, n is in the range from 0 to 50, preferably 0 to 10, and K is a bifunctional linker moiety; c) providing a solid phase having polyamine groups bound thereto; d) coupling said linker-connected dianhydride to said carrier via an amino group of a polyamine group bound to the solid phase, wherein a single carboxy group per APA reacts with the amine moiety and the other anhydride group remains unchanged; e) providing water or an aqueous puffer to hydrolyze the remaining anhydride groups.

Also disclosed is a method for producing a solid-phase chelator material having branched chelating groups comprising APA groups connected via a trifunctional linker as described, comprising the following steps: a) mixing an APA dianhydride and a trifunctional linker L in a ratio of 3:1 to 9:4, preferably 3:1 to 5:2, and a solid phase with bound polyamine groups; b) coupling the APA dianhydride to a solid-phase carrier via amine group onto the linker, wherein the linker reacts with three different dianhydrides, so that a reaction product of one of the following formulas is formed,

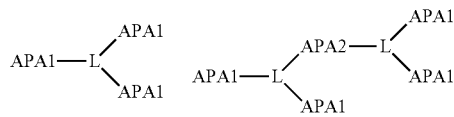

wherein APA1 is an APA group with one anhydride group and one amide group, APA2 is an APA with two amide groups and Lisa trifunctional linker moiety; c) providing a solid phase comprising polyamine groups; d) coupling said linker-connected APA to said carrier via amide group onto the polyamine-modified solid phase, wherein a single carboxy group per aminopolycarboxylic acid reacts with the amine moiety and the other anhydride groups remain unchanged; and e) providing water or an aqueous puffer to hydrolyze the remaining anhydride groups.

Also provided is a method for producing a metal ion load solid-phase chelator material comprising carrying out as described for producing a solid-phase chelator material and then immobilizing metal ions by contacting the solid-phase chelator material with a solution of metal ions which are selected from the group consisting of $Ni^{2+}$, $Co^{2+}$, $Cu^{2+}$, $Zn^{2+}$, $Al^{3+}$, $Fe^{3+}$, $Eu^{3+}$, $Ga^{3++}$, $Mn^{2+}$, $Ca^{2+}$.

Also provided is the use of the solid-phase chelator material or the metal ion loaded solid-phase chelator material or the solid-phase chelator material produced with the method or the metal ion loaded solid-phase chelator material produced with the method in the field of molecular biology, for the purification of proteins with a plurality of histidine residues, the purification of membrane proteins with a plurality of histidine residues, the purification of GPCRs with a plurality of histidine residues, the purification of transporter proteins with a plurality of histidine residues, the purification of proteins for therapeutic uses, the purification of recombinant proteins or polypeptides with a plurality of histidine moieties, the purification of phosphoproteins, the purification of metalloproteins, the purification of nucleic acids and/or for immobilized metal affinity chromatography (IMAC).

Also provided is a method for purifying a biomolecule, in particular a recombinant protein or polypeptide, comprising the steps of: a) providing a metal loaded solid-phase chelator material or as produced with the method; b) providing a sample containing the biomolecule, in particular a protein or polypeptide with a plurality of histidine moieties, c) contacting the sample with the metal loaded solid-phase chelator material; d) separating the bound polypeptide or protein from the solution; e) eluting the recombinant protein or polypeptide form the solid phase.

In some embodiments, the protein is selected from the group consisting of membrane proteins, GPCRs and antigens.

In some embodiments, EDTA and imidazole are added to the binding buffer in a concentration of at least 20 mM, and DTT is added in a concentration of at least 10 mM, without interfering the metal binding and the protein yield.

In some embodiments, the solid-phase immobilized aminopolycarboxylic acid compound according to the preceding claims can be washed with a sodium hydroxide solution in order to remove contaminants and sticking proteins to regenerate the material for further biomolecule purification and still has a protein binding capacity of at least 50 mg per ml.

DETAILED DESCRIPTION

Figure 1:
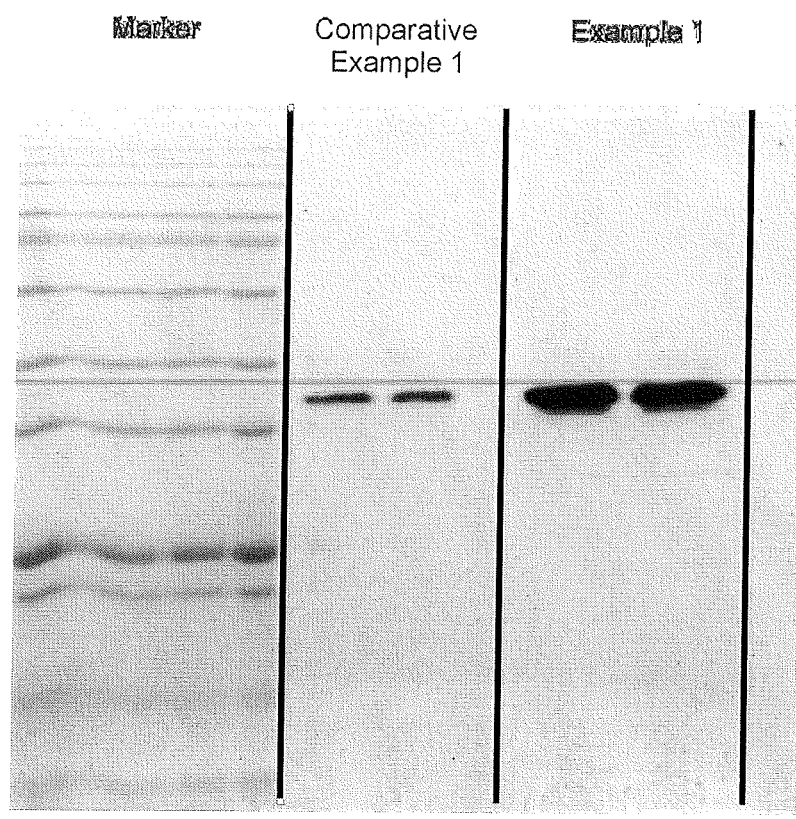
FIG. 1 is a picture of a gel of eluates obtained in affinity purifying experiments with a solid-phase chelator material according to example 1 and to a comparative example.
Figure 2:
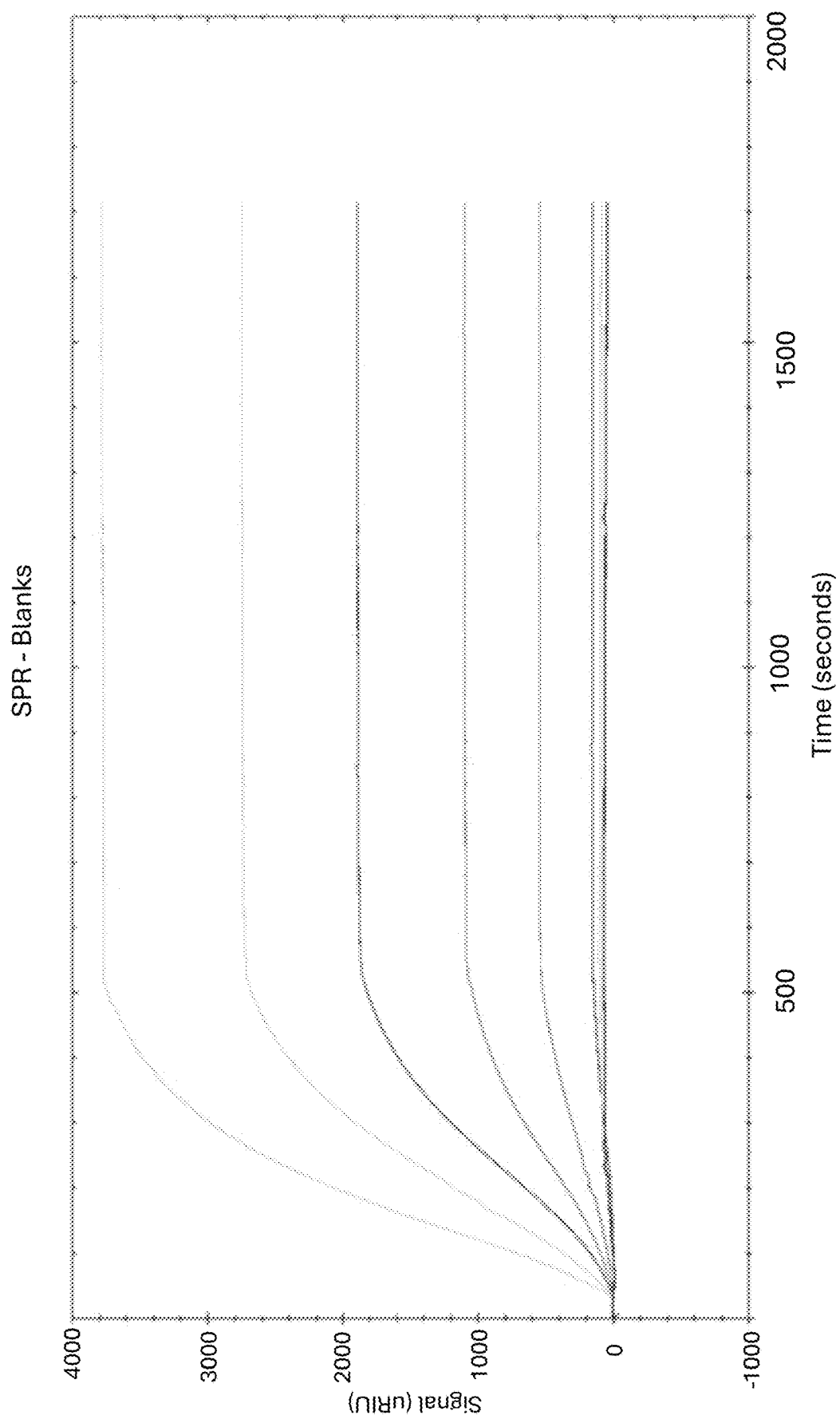
FIG. 2 is a graph showing results of an affinity measurement with Surface Plasmon Resonance for a chelator modified chip of the present invention.
Figure 3:
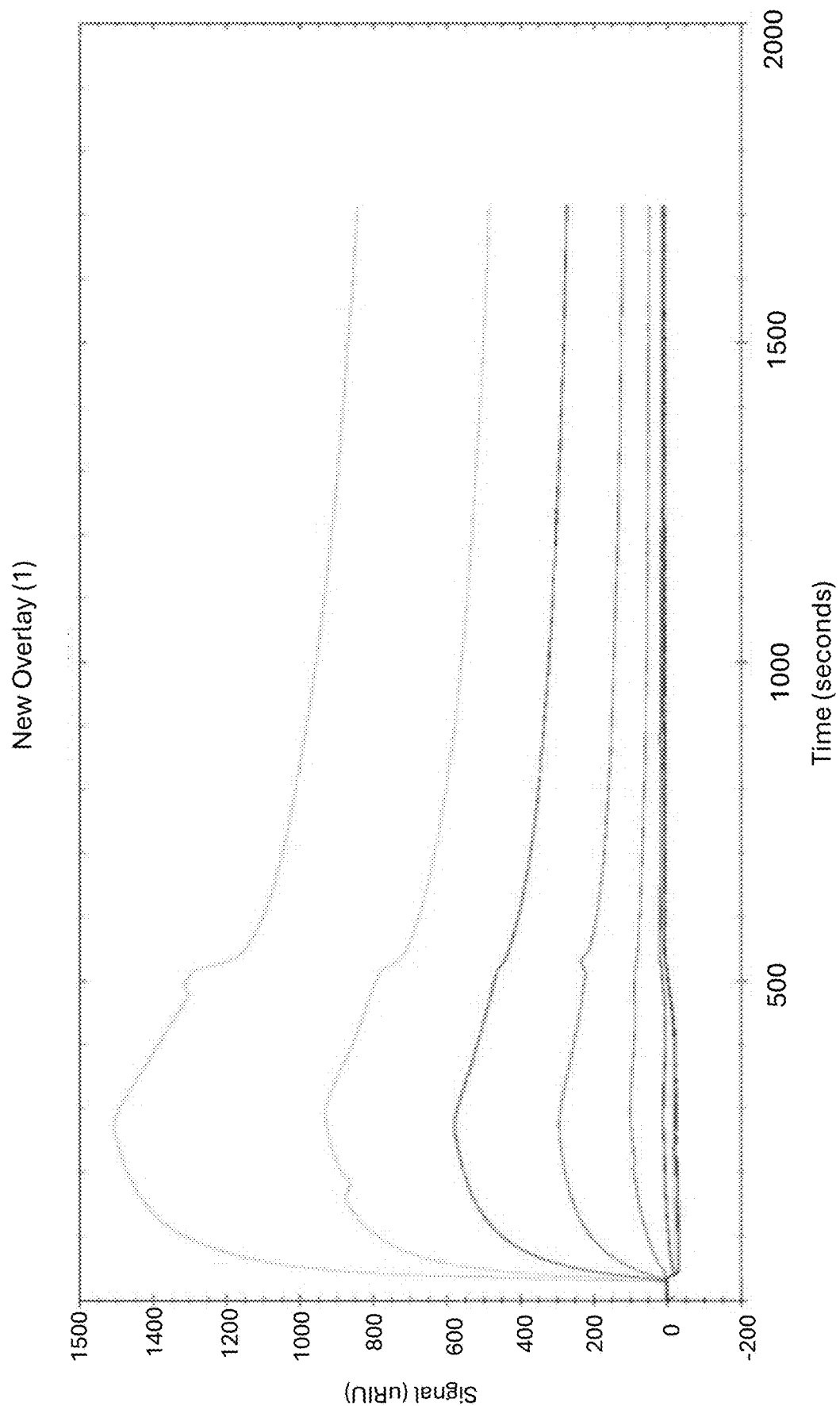
FIG. 3 is a graph showing the results of an affinity measurement with Surface Plasmon Resonance for Ni-NTA (comparative example 2).

The present invention provides a solid-phase chelator material and a metal loaded solid-phase chelator material showing inter alia a high stability against alkaline solutions.

Furthermore, the present invention provides an easy and convenient method for producing such a solid-phase material.

Furthermore, the present invention provides a method for purifying proteins and the use of a solid-phase chelator material for purifying proteins, in particular recombinant proteins.

According to a first aspect the present invention provides a solid-phase chelator material comprising a solid phase, polyamine groups bound to the solid phase and chelating groups bound to the polyamine groups, wherein at least a part of the polyamine groups are connected with at least two chelating groups per polyamine group and wherein each chelating group comprises one or several aminopolycarboxylic acid groups (APA groups), with the proviso that the number of APA groups per polyamine group connected with at least two chelating groups is at least three.

A polyamine group in the sense of the invention is a group which is derived from a polyamine. A polyamine is an organic molecule comprising several primary or secondary amino groups, preferably at least three, more preferably at least four primary and/or secondary amino groups. At least a part of these amino groups, in preferred embodiments all of these amino groups are reacted with reactive groups on the solid phase and/or with reactive groups of chelating group precursors during the synthesis of the solid-phase chelator materials. Reaction of these amino groups may lead to the formation of secondary or tertiary amino groups or amide groups. The polyamine may comprise further functional groups, e. g. hydroxyl groups, which may be usable for covalently binding the polyamine to the solid phase.

A chelating group in the sense of the invention is a group which is derived from a chelating group precursor. The chelating group precursor may be a single chelator molecule or chelator, e.g. an EDTA molecule, or a combination of at least two or three chelator molecules, which are covalently connected with each other, preferably by means of linker moieties. The chelating group precursor may be non-activated or may be activated, for example by means of organic acid anhydride group(s).

The term "at least a part of the polyamine groups" as used above has to be understood in that all polyamine groups are connected with at least two chelating groups per polyamine group or only a part of the polyamine groups are connected with at least two chelating groups per polyamine group. The amount of polyamine groups having at least two chelating groups may inter alia be controlled via the amount of the different reaction partners during the synthesis of the solid-phase chelator materials of the invention. Preferably a majority or all of the polyamine groups are connected with at least two chelating groups.

Preferably, the chelating groups are selected from the group consisting of individual APA groups, linear chelator chains formed by two or more APA groups which are connected with each other via bifunctional linker moieties K, branched chelator chains formed by three or more APA groups connected with each other via trifunctional linker moieties L, and mixed chelator chains formed by four or more APA groups connected with each other via at least one bifunctional linker moiety K and at least one trifunctional linker moiety L.

The number of chelating groups bound to a polyamine group is preferably at least three, more preferably at least four.

The number of APA groups which are coupled to a polyamine group connected with at least two chelating groups is preferably in the range from 3 to 20, more preferably in the range from 4 to 15. The at least three APA groups may be at least three monomeric APA groups or chelator groups, which are individually bound to the polyamine group, or they may be organized in linear and/or branched chelator chains thereby forming dimeric, trimeric, tetrameric, . . . , multimeric chelator groups.

According to a definition of the IUPAC "chelator" means a polydentate ligand which can be involved in the formation of at least two coordinative bonds.

In this invention the chelators are aminopolycarboxylic acids (APAs). Preferably used are APAs selected from the group consisting of EDTA (ethylenediamine tetraacetic acid), DTPA (diethylene triamine pentaacetic acid), TTHA (triethylenetetramine hexaacetic acid), EDDS (Ethylenediamine-N,N'-disuccinic acid), DOTA (1,4,7,10-tetraazacyclododecane-1,4,7,10-tetraacetic acid), NOTA (1,4,7-triazacyclononane-triacetic acid).

One carboxy group of the first chelator is coupled to the solid phase via amide bond. Another carboxy group of the first chelator is coupled with a linker via amide, and the linker is covalently coupled to a second or even to a third chelator, so that the chelator is bound to the solid phase in linear or branched chains, bound to a solid phase via a single carboxy group of only one chelator per molecule. So only one modified chelator per chain is bound to the solid phase, so that the sterical demand of the chelator chains is comparable with a single chelator. This leads to a high density of chelators on the solid phase and, together with a comparative effect of the neighboring chelating groups, to a high binding capacity, as well as to a high affinity for his-tagged proteins, compared to proteins without his-tag.

In the present invention the carboxylic acid groups are written in the acid form, but with a pH between 6 and 8.5, which is common for the affinity purification of recombinant proteins, the biggest part of the carboxylic acid groups are in the carboxylate form, and some amino groups are protonated. In order to keep the description simple and clear, in the text and claims these groups are written as "COOH" and $NH_2$.

Preferably, the polyamine groups are derived from polyamines selected from the group consisting of diethylene triamine, triethylene tetramine, tetraethylene pentamine, penta-ethylene hexamine, linear and branched polyethylene imine, poly-lysine, polypropylene imine, macrocyclic polyamines like cyclam, cyclen, and 1,4,7-triazacyclononane, branched polyamines like 1,1,1-tris(aminomethyl) ethane, tris-aminoethyl amine, tris aminopropyl amine, tetrakis-ethylamino amine, tetrakis-ethylamino amine, tetrakis-aminopropyl amine, and amine functionalized tetrafunctional branched PEGs, basing on a pentaerithritol core.

More preferably, the polyamine groups are derived from polyamines selected from the group consisting of diethylene triamine, triethylene tetramine, tetraethylene pentamine and pentaethylene hexamine.

Even more preferably, the polyamine groups are derived from polyamines selected from the group consisting of triethylene tetramine, tetraethylene pentamine and pentaethylene hexamine.

The polyamine groups may contain other functional groups, such as carboxylic acids, hydroxy groups, and the like, as long as they do not influence the functionality.

In preferred embodiments of the invention, the chelating groups may have
the general formula -(APA1-K)$_n$-APA2 in which APA1 and APA2 are identical or different from each other, n is an integer in the range from 1 to 50 and K is a bifunctional linker moiety; and/or the general formula 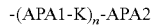

and/or the general formula 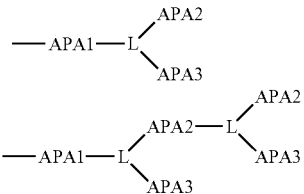

in which APA1, APA2 and APA3 are aminopolycarboxylic acid groups which are identical or different from each other and L is a trifunctional linker moiety.

Accordingly, in preferred solid phase chelator materials of the invention the chelating groups may be individual APA groups, linear chelating groups comprising at least two APA groups which are connected via bifunctional linker moieties K, branched chelating groups comprising at least three APA groups which are connected via trifunctional linker moieties L, or combination of said different types of chelating groups.

Furthermore, it is preferred that the APAs and the linker moieties are connected with each other via amide moieties and/or that the chelating groups and the polyamine groups are connected with each other via amide moieties.

The chelating groups of the solid-phase chelator material of the invention may comprises one or several bifunctional linker moieties K and/or one or several trifunctional linker moieties L.

According to the invention, the bifunctional linker moiety K may be selected from the group consisting of A-(CH$_2$)$_n$—B, A-Q-B and A-(C$_2$H$_4$O)$_m$—(CH$_2$)$_n$—B. In these formulas A and B are functional groups which are able react with carboxy groups, namely OH, NH$_2$, NHR, Cl, Br, I, OMs, OTs, N$_3$. They are preferably selected from NH$_2$ and NHR. R may be a hydrocarbon group with the formula C$_n$H$_{2n+1}$, in which n is in the range from 1 to 6. m is an integer in the range from 1 to 12, n is an integer in the range from 2 to 12. Q is a straight or branched configuration of 2-100 atoms, optionally containing C, H, N, O and S, including cyclic compounds, such as carbohydrates.

The bifunctional linker K may be in particular a diamine. Preferably, the bifunctional linker moiety K is selected from the group consisting of ethylenediamine, 1,4-diaminobutane, 1,6-diaminohexane, 1,8-diaminooctane, and polyetheramines, like α,ω-amino-functionalized polypropylene glycol compounds, such as Jeffamine ED 600 (Huntsman, The Woodlands, TX, USA).

Preferably, the trifunctional linker moiety L may have one of the general formulas

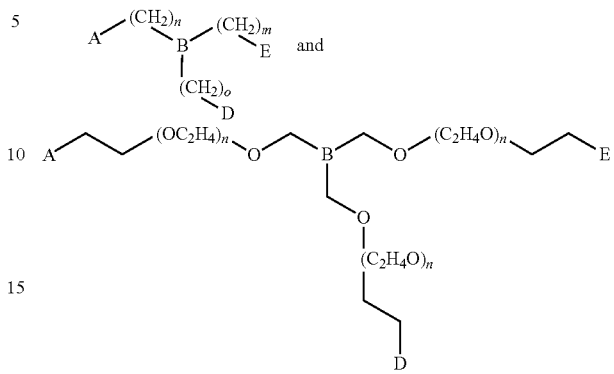

in which A, D and E are functional groups which are able to react with a carboxy group, preferably —NH$_2$ or —NHR, B is a branching atom, preferably C or N, which is connected with at least three stable bonds preferably to carbon atoms, connected with functional groups, n, m and o are integers in the range from 2 to 30. Preferably the trifunctional linker moiety L is a triamine. More preferably, the trifunctional linker moiety L is selected from the group consisting of diethylene triamine, 1,1,1-tris(2-aminoethyl)amine, tris(3-aminopropyl)amine, and amino-functionalized trifunctional branched PEGs based on a glycerol core.

Preferably, the linkers used for synthesis of multimeric aminopolycarboxylic acid resins are selected from ethylene diamine, 1,3-diaminopropane tris(3-aminopropyl)-amine, tris(2-aminoethyl)amine, and/or diethylenetriamine.

The solid-phase chelator material of the present invention may have a spacer moiety S which is inserted between the solid phase and the polyamine groups. The spacer moiety is preferably derived from a compound which is selected from the group consisting of epichlorohydrine, epibromohydrine, 1,2-ethylene glycol diglycidyl ether, 1,4-butanediol diglycidyl ether, allyl glycidyl ether and allyl bromide. The spacer moiety may be coupled to the solid phase via an ether bond and to the adjacent aminopolycarboxylic acid via an amide bond.

Preferably, the solid phase is selected from the group consisting of agarose, cellulose, agar, dextran, chitosan, alginate, gellan, preferably agarose, which are chromatographic supports. For an optimized covalent coupling of the chelating groups the solid phase is preferably polyamine-functionalized.

Alternatively, the solid phase can comprise porous or non-porous silica, aluminum oxide, titanium oxide, zirconium oxide, other metal- or semi-metal-oxides or the like, preferably silica. Other solid phases contain gold layers, glass, polymers such as polystyrene, methacrylates, acrylates, acrylamide, vinyl acetate, vinyl alcohol or the like.

The solid phase can be, but is not limited to a porous or non-porous particle, magnetic silica, agarose, polystyrene, styrene derivatives, acrylate, methacrylate or polyvinyl alcohol particle.

Preferably, the solid phase may be a sensor surface, a membrane, a non-porous chromatographic support, a porous chromatographic support, a coated tube, a coated surface, e. g. a coated plastic surface of an Eppendorf or falcon polypropylene tube, a coated microtiter plate, array plates, microarray surfaces.

According to the invention, the solid phase may be preferably selected from magnetic agarose, magnetic silica and a magnetic polymer. More preferably, it is magnetic agarose.

According to the invention, the solid phase may be preferably selected from dextran modified gold-chips and magnetic beads.

For a person skilled in the art there are many ways to prepare amine modified agarose, such as reacting with epichlorohydrine and chemical reaction with a poly amine. Alternatively, carboxymethylated agarose, obtained by reaction with sodium chloroacetate is being modified to amines by reaction with polyamines. The chemical reaction of the amino groups with the carboxy functions of the chelators can be done via activation with EDC or other condensing agents, or by direct contact of the chelator anhydride with the polyamine. Third of all an allyl functionalization could be created by reacting agarose with allyl glycidyl ether or allyl bromide. After bromination of the double bond, the halogenide could react with a polyamine.

Amine-modified silica, glass and other metal oxides can be prepared by e.g. coating with 3-glycidyltriethoxysilane and reactions with polyamines. Gold surfaces can be modified by coating long, thiol-functionalized linear molecules, so-called "self-assembling monolayer", which can be polyamine functionalized.

The solid-phase chelator materials according to the present invention are preferably materials with aminopolycarboxylic acid molecules, consisting of a chain of chelators, or a branched chelator molecule, covalently bound to a solid phase. The chelator chains are formed by coupling chelators with linker molecules, where the chain length can be regulated.

According to a second aspect, the present invention relates to a metal ion loaded solid-phase chelator material. This metal ion chelator material comprising one of the above described solid-phase chelator materials and is loaded with metal ions selected from the group consisting of $Ni^{2+}$, $Co^{2+}$, $Cu^{2+}$, $Zn^{2+}$, $Al^{3+}$, $Fe^{3+}$, $Eu^{3+}$, $Ga^{3+}$, $Mn^{2+}$, and $Ca^{2+}$.

According to a third aspect the present invention relates to a method for producing above defined solid-phase chelator material.

A first variant of the method of the invention comprises covalently binding at least three monomeric APAs on a solid phase having polyamine groups bound thereto under formation of polyamine groups having at least three monomeric APA groups bound thereto via an amide group.

A second variant of the method of the invention comprises covalently binding at least two APAs on a solid phase having polyamine groups bound thereto under formation of a solid-phase material with polyamine groups having at least two APA groups bound thereto via an amide group, adding a bifunctional linker K or a trifunctional linker L to said solid-phase material, reacting said coupled linker with a carboxy group of a second APA, thereby forming a solid-phase chelator material of APA groups which are bound to the polyamine groups. The polyamine groups are bound to the solid phase, optionally repeating the steps of adding a linker and then adding a further APA for extending the length of the linear chelator chains or the branched chelator chains. The chelating groups produced in this way are in the form of linear chelator chains or branched chelator chains.

A third variant of the method of the present invention comprises reacting at least two monomeric APAs with a bifunctional linker K or at least three monomeric APAs with a trifunctional linker L under formation of a multimeric APA chelator comprising a linear chelator chain or a branched chelator chain and covalently binding at least two multimeric APA chelators on a solid phase having polyamine groups bound thereto under formation of polyamine groups having at least two linear and/or branched chelator chains bound thereto via an amide group.

a) Preferably, a method for producing a solid-phase chelator material having linear chelating groups with APA groups connected via a bifunctional linker comprises the following steps: providing an APA and a solid phase having polyamine groups bound thereto;

b) coupling the APA with the solid phase in the presence of a condensing agent, wherein a single carboxy group of the APA reacts with the solid phase under binding of the APA to the solid phase;

c) mixing the solid-phase material obtained in step b) with a bifunctional linker K;

d) coupling the bifunctional linker K with an APA carboxy group in the presence of a condensing agent, wherein a single reactive group of the bifunctional linker K reacts with the bound APA;

e) mixing the solid-phase material obtained in step d) with a further APA;

f) coupling the further APA with the bifunctional linker in the presence of a condensing agent, wherein a single carboxy group of the further APA reacts with a further reactive group of the bifunctional linker K bound to the solid-phase material;

g) optionally repeating step c) to f) at least one time.

Preferably, a method for producing a solid-phase chelator material having linear chelating groups with APA groups connected via a bifunctional linker comprises the following steps:

a) providing an APA dianhydride and a solid-phase material having polyamine groups bound thereto;

b) coupling said APA dianhydride with said solid-phase material via an amino group of bound polyamine, wherein a single anhydride group per APA dianhydride reacts with an amino moiety and the other anhydride group remains unchanged;

c) washing the solid-phase material obtained in step b) with an anhydrous solvent in order to remove the non-coupled dianhydride;

d) providing the solid-phase material obtained in step c) and a bifunctional linker K;

e) coupling the bifunctional linker K with the APA anhydride group, wherein a single amine group of the bifunctional linker K reacts with the APA anhydride group and the other functional group of the bifunctional linker K remains unchanged;

f) washing the solid phase with an anhydrous solvent in order to remove the non-coupled linker molecules;

g) providing the solid-phase material obtained in step f) and additional APA dianhydride;

h) coupling said APA dianhydride to said bifunctional linker K, wherein a single carboxy group per APA reacts with the remaining functional group of the bifunctional linker K;

i) optionally repeating step c) to h) at least one time.

In the above described methods of the invention water or an aqueous buffer may be added in a final step for hydrolyzing remaining anhydride groups.

Preferably, a method for producing a solid-phase chelator material having linear chelating groups with APA groups connected via a bifunctional linker comprises the following steps:

a) providing an APA dianhydride and a bifunctional linker K in a ratio of 2:1 to 1:1, preferably 2:1 to 1.25:1;

b) coupling the APA dianhydride to said bifunctional linker K via an amine or a hydroxy group on the linker, wherein the linker reacts with two different dianhydrides, so that a substance APA1-K-(APA2-K)$_n$-APA3 is formed, wherein APA1 is an APA with one anhydride group and one amide function, APA2 is an APA with two amide functions, and APA3 is an APA with one anhydride group, n is in the range from 0 to 50, preferably 0 to 10, K is a bifunctional linker moiety;
c) providing a solid phase having polyamine groups bound thereto;
d) coupling said linker-connected dianhydride to said carrier via an amino group of a polyamine group bound to the solid phase, wherein a single carboxy group per APA reacts with the amine moiety and the other anhydride group remains unchanged;
e) providing water or an aqueous buffer to hydrolyze the remaining anhydride groups.

Preferably, a method for producing a solid-phase chelator material having branchend chelating groups with APA groups connected via a trifunctional linker comprises the following steps:
a) mixing an APA dianhydride and a trifunctional linker in a ratio of 3:1 to 9:4, preferably 3:1 to 5:2, and a solid phase with bound polyamine groups;
b) coupling the APA dianhydride to a solid-phase carrier via amine group onto the linker, wherein the linker reacts with three different dianhydrides, so that a reaction product of one of the following formulas is formed,

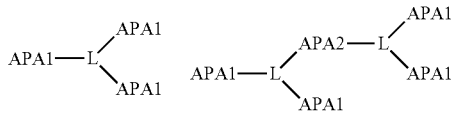

wherein APA1 is an APA group with one anhydride group and one amide group, APA2 is an APA with two amide groups, and L is a trifunctional linker moiety;
c) providing a solid phase comprising polyamine groups;
d) coupling said linker-connected APA to said carrier via amide group onto the polyamine-modified solid phase, wherein a single carboxys group per aminopolycarboxylic acid reacts with the amine moiety and the other anhydride groups remain unchanged;
e) providing water or an aqueous puffer to hydrolyze the remaining anhydride groups;

Furthermore, the present invention includes a method of preparing a solid-phase bound material usable for the affinity purification of proteins, where a plurality of aminopolycarboxylic acid molecules is coupled via amide groups. The aminopolycarboxylic acids consist of chelators, connected to other chelators via di- or trifunctional linkers. Examples for this invention can be described by the formulas:

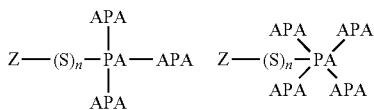

wherein Z is a solid phase, S is an optional spacer molecule able to bind both to the solid phase and the chelator, n is 0 or 1, PA is a polyamine, APA is a aminopolycarboxylic acid or a linear chain or a branched chain of APA groups connected with each other by means of bifunctional linker moieties K and/or trifunctional linker moieties L.

In these formulas three and four aminopolycarboxylic acid molecules are coupled to one polyamine, but the number of aminopolycarboxylic acid molecules could also be higher, such as five, six or even more, dependent on the polyamine and the number of existing amino groups per polyamine molecule.

According to a fourth aspect the present invention relates to a method for producing a metal ion load solid-phase chelator material. This method comprises carrying out one of the above described methods for producing a solid-phase chelator material and then immobilizing metal ions by contacting the solid-phase chelator material with a solution of metal ions which are selected from the group consisting of $Ni^{2+}$, $Co^{2+}$, $Cu^{2+}$, $Zn^{2+}$, $Al^{3+}$, $Fe^{3+}$, $Eu^{3+}$, $Ga^{3++}$, $Mn^{2+}$, $Ca^{2+}$.

According to a fifth aspect the present invention relates to the use of the above described solid-phase chelator material or the solid-phase chelator material obtained according to one of the above described methods in the field of molecular biology, for the purification of proteins with a plurality of histidine residues, the purification of membrane proteins with a plurality of histidine residues, the purification of GPCRs with a plurality of histidine residues, the purification of transporter proteins with a plurality of histidine residues and/or the purification of proteins for therapeutic uses.

According to a sixth aspect the present invention relates to a method for purifying a recombinant protein or polypeptide, comprising the steps:
a) providing a metal loaded solid-phase chelator material as described further above or as obtained according to a method described further above;
b) providing a sample containing a protein or polypeptide with a plurality of histidine moieties,
c) contacting the sample with the metal loaded solid-phase chelator material;
d) separating the bound polypeptide or protein from the solution;
e) eluting the recombinant protein or polypeptide form the solid phase.

Preferably, in the above method the protein is selected from the group consisting of membrane proteins, GPCRs and antigens.

Preferably, in the above method EDTA and imidazole are added to the binding buffer in a concentration of at least 20 mM, and DTT is added in a concentration of at least 10 mM, without interfering the metal binding and the protein yield.

Preferably, in the above method the solid-phase immobilized aminopolycarboxylic acid compound according to the preceding claims can be washed with a sodium hydroxide solution in order to remove contaminants and sticking proteins to regenerate the material for further biomolecule purification and still has a protein binding capacity of at least 50 mg per ml.

As already mentioned further above, there are essentially two ways to prepare a substance according to this invention:
a) At first covalently coupling of the first chelator onto a polyamine modified solid phase, then coupling one end of a bi- or trifunctional linker to the chelator, reacting said linker with a carboxy group of a second chelator, and, optionally, coupling of a second linker to the second chelator via a carboxylic acid function, adding a third chelator, which reacts with the second linker, and so on:
b) Preparation of a multimeric chelator by reacting at least two monomeric chelators with di- or trifunctional linker, and subsequent coupling of the multimeric chelator onto a polyamine modified solid phase via one carboxylic acid function.

The number of bound chelators can be determined by different approaches for both ways, evident for a person skilled in the art:
a) The number of repeating steps for coupling the chelator and the linker molecules regulates the chelator chain length in way a). So by sequentially coupling of chelator, linker and chelator a dimeric chelator is obtained, while by sequentially coupling of chelator, linker, chelator, linker and chelator a trimeric chelator is prepared.
b) The ratio of linker to chelator influences the chain length of the chelator-linker-chain for way b). So, for instance, when a linker is slowly added to a solution of the chelator in the ratio 1:2, a molecule with the formula Ch-L-Ch is obtained, while, when adding a linker to the chelator in the ratio 2:3, a substance with the formula Ch-L-Ch-L-Ch is generated (L means linker and Ch means chelator). When adding a linker to chelator in the ration 1:1, long chains (Ch-L)$_n$ are formed, as described e.g. in Reactive and Functional Polymers, 29 (1996) 29-39 by Brosse et al.

One method to couple the chelator onto the solid phase or linker contains activation of the chelator by carbodiimide chemistry with e.g. EDC, or with other condensing agents, such as carbonyl imidazole, disuccinimidyl carbonate, and other peptide bond forming agents, such as PyBOP and HBTU, and the like, and mixing of the reactants. It is also feasible to add the linker to the activated chelator, as well as the activated chelator to the linker. The linker can also be activated for coupling onto carboxy groups via transformation to tosyl, triflate- or mesyl functionalities, or the like. A good overview of common methods can be found in Hermanson et al., Bioconjugate Techniques, 3$^{rd}$ edition, ISBN: 978-0-12-382239-0.

Another way of forming chelator chains is basing on addition of linker or the solid phase to a solution of chelator dianhydride preferably in an aprotic solvent, such as 1,4-dioxane, N, N-dimethylformamide, dimethyl sulfoxide, diethyl ether, or tetrahydrofuran. Examples for these anhydrides are EDTA anhydride, DTPA anhydride, and TTHA anhydride. Coupling of an amino group with an anhydride leads to the formation of an amide bond.

After synthesis and coupling of the chelator chains the reaction product can be charged with metal ions, which can bind the desired target proteins. As Ni, Cu, Co, Zn, Fe, Eu, Sc are suitable for reversible protein binding, nickel and cobalt are preferred for purification of his-tagged proteins, while iron and alumina are preferred for the isolation of phosphoproteins. For instance regarding IMAC of poly-his proteins, the affinity of the metal follows the sequence Cu>Ni>Zn>Co, while specificity of the purification follows the sequence Cu<Ni<Zn<Co.

Polyhistidine-tags are common in molecular biology and can be used for separating recombinant proteins, expressed in bacteria, such as E coli, yeast, and mammalia. So his-tagged proteins bind with metal ion-loaded chelators at pH values, where the histidine groups are non-protonated, while the great majority of the remaining proteins don't interact with the metal ions. When the pH value is lowered and histidine becomes protonated, the interaction of the protein to the metal ion is cleared, and the protein can be eluted from the column. Alternatively, the elution can also be performed with applying high concentrations of imidazole, which binds onto the metal ions and replaces the his-tags, which leads to elution of the protein. For this application, imidazole concentrations of 100 to 300 mM are commonly used.

As mentioned earlier, e.g. Cu-IDA and Ni-NTA were used with chromatography materials to purify recombinant his-tagged proteins from a mixture of biological compounds. The solid-phase immobilized aminopolycarboxylic acid compound, according to this invention, can also be used for metal affinity purification of his-tagged proteins. Due to the fact, that the chelators are connected with linkers to chain-like molecules with only one connection to the solid phase, the steric demand is comparable to mono-EDTA, while the number of chelators immobilized is much higher. So the metal binding capacity, determined with $Cu^{2+}$, shows very high values, so 50-80 µmol/ml can be reached. In addition to that, extremely high quantities of his-tagged proteins can be purified with the material according to this invention. So, in the following examples capacities of up to 80 mg protein per ml can be obtained.

Moreover, because of the short distance between the chelators and adjacent metal ions, they are able to bind his-tagged proteins with a cooperative effect, which gives a much higher affinity than monomeric chelators. And although a mixture of tetradentate (hexadentate like EDTA with two amide functions instead of carboxylic acid) and pentadentate (hexadentate like EDTA with one amide function instead of carboxylic acid) chelators is used, due to the strong affinity binding, the material according to this invention shows an extremely good resistance against solution-based chelating agents and reductants. So these extremely high protein binding capacities are also maintained with drastic conditions, e.g. when 20 mM Imidazol, 20 mM EDTA, and 10 mM DTT are added to the binding buffer.

Due to the high resistance against chelators and reductants the material according to this invention is particularly suitable for the purification of membrane proteins, especially GPCRs. For the membrane protein purification in many cases detergents, such as dodecyl maltoside, or n-tetradecyl phosphocholine (FOS-14) are used to stabilize the protein in aqueous solution against precipitation and denaturation. In an experiment the material according to this invention has been tested for the purification of membrane proteins, and it showed high binding capacity and a good tolerance against detergents.

In order to work with an economical purification procedure, especially, when packed columns are used, it is desirable to develop a purification resin, which can be regenerated with a solution, which can remove contaminants from further purifications and allows the use of the resin for other purification runs without contaminations. In general, persons skilled in the art use sodium hydroxide solution with a concentration of 100 mM to 500 mM, which effectively removes precipitated and non-specifically bound proteins from affinity columns. During synthesis of the materials according to this invention, it was surprisingly found, that even after a protein purification run and a hydroxide solution treatment, the binding capacity of this resin was still very high and significantly higher than with other comparable materials. So even after repeated treatment with 0.5 M NaOH for 5 minutes, a protein binding capacity of at least 50 µm per ml resin could be maintained.

The specific phosphorylation of serine, threonine, or tyrosine residues is the most common mechanism for the regulation of cellular protein activity. Kinases catalyze the addition of a phosphate moiety to the hydroxyl group of the respective amino acid. The activity of protein kinases is regulated by various intracellular key signals, e.g., the concentration of cyclic AMP or Ca2+. Phosphatases catalyze the specific dephosphorylation of protein, allowing enzymes to switch between phosphorylated and dephosphorylated states.

Reversible protein phosphorylation has been known for some years to control a wide range of cellular processes and activities such as transmembrane signaling, intracellular amplification of signals, and cell-cycle control. The analysis of such phosphorylated residues forms the core of signal-transduction studies. With the material, loaded with aluminum, iron, gallium, or europium ions, a complete separation of phosphorylated from unphosphorylated cellular protein fraction is feasible. The affinity chromatography procedure, in which phosphorylated proteins are bound to a column while unphosphorylated proteins are recovered in the flow-through fraction, reduces complexity and greatly facilitates phosphorylation-profile studies. Both fractions retain full biological activity and can be further purified if desired.

Proteins that carry a phosphate group on any amino acid are bound with high specificity to the solid phase, while proteins without phosphate groups do not bind to the resin and can therefore be found in the flow-through.

For the purification a gentle lysis procedure is carried out in a 25 mM MES buffer, pH 6.0, that contains CHAPS, a zwitterionic detergent, protease inhibitors, and, optionally, benzonase or another DNase or RNase in order to remove protein-nucleic acid complexes. The washing steps are performed with lysis buffer, and the purified phosphoprotein is eluted with potassium phosphate buffer, pH 7.5. With this procedure, the material according to this invention allows an effective purification even in the presence of strong chelators and reductants.

Also metal-binding proteins show affinity to IMAC resins, given that the suitable metal cation is immobilized. So the affinity of different immobilized metal ions against zinc finger domains was examined in protein Expr. Purif. 2011, 79(1): 88-95, and it turned out, that different affinities could be monitored, depending from the element. Copper-binding proteins can be purified using Cu— and Zn IMAC columns, as presented in Proteomics, 2006, May; 6(9):2746-2758. The high ligand density together with a strong binding to metal cations give the material according to this invention a high potential for this application.

Moreover, metal ion-loaded chelator resins are suited for nucleic acid purification. In Biotechnol. Prog. 2005, 21, 1472-1477 a method of separating single- and double-stranded nucleic acids is presented. The principle of this procedure is basing upon reversible adsorption of imidazyl moieties onto immobilized metal ions. So partially denatured genomic DNA can be bound to IMAC resin, while double-stranded plasmid DNA, without accessible imidazyl groups of purine bases, cannot be immobilized. With this method, a 1.000.000 fold clearance could be achieved by using Cu IDA agarose. Further applications contain the removal of PCR error products, as described in Plos ONE, 2011, 6, 1, e15412. The extraordinary high stability and affinity of the material according to this invention makes this material suitable for this application.

A further application of the inventive material is the removal of metal ions from solutions. EDTA forms metal complexes with stability constants of about 14 to 25 (Martell A. E. & Smith R. M. (1982), Critical Stability Constants, Vol. 5: First Supplement, Plenum Press, New York), so a aminopolycarboxylic acid chain-modified solid phase can efficiently be used to bind metal ions, such as $Ni^{2+}$, $Co^{2+}$, $Mn^{2+}$, $Cr^{2+}$, $Pb^{2+}$ and to drastically reduce their concentration in a solution by simply contacting the chelator-bound resin with the liquid. One example is the use of chelator-modified agarose particles, which can be filled into a cartridge, and the heavy metal concentration of the liquid is reduced during passing through the column. In addition to that, the chelator chains can be coupled to magnetic agarose particles, which can be added to a solution, mixed and removed by a magnetic separator after binding to metal ions.

According to a further aspect of the present invention the solid-phase immobilized aminopolycarboxylic acid compound consists of a solid phase, spacer molecules, polyamines bound to the spacer molecule, and a plurality of aminopolycarboxylic acids covalently coupled to the polyamines.

Preferably, in said aminopolycarboxylic compound the spacer is coupled to the solid phase via ether bonds, and to the adjacent aminopolycarboxylic acid via amide.

Preferably, in said aminopolycarboxylic acid compound the adjacent aminopolycarboxylic acid is immobilized on the solid phase via amide bond.

Preferably, in said aminopolycarboxylic compound the number of aminopolycarboxylic acids coupled to a polyamine is 3 to 20.

Preferably, in said aminopolycarboxylic compound the number of aminopolycarboxylic acids coupled to a polyamine is 4 to 15.

Preferably, in said aminopolycarboxylic compound the spacer is prepared by coupling epichlorohydrine, epibromohydrine,1-2-ethylene glycol diglycidyl ether, 1,4-butanediol diglycidyl ether on agarose.

Preferably, in said aminopolycarboxylic compound the spacer is prepared by coupling allyl glycidyl ether, or allyl bromide on agarose and subsequent bromination.

Preferably, in said aminopolycarboxylic compound the aminopolycarboxylic acids have the general formula:

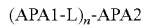

wherein APA1 is a hexadentate chelator, coupled via two amide functions, APA2 is a hexadentate chelator, L is a linker molecule, coupled to APA1 and APA2 via amide function, n is 1-50.

Preferably, in said aminopolycarboxylic compound the linker molecule is a diamine.

Preferably, in said aminopolycarboxylic compound the linker molecule is selected from the group ethylene diamine, 1,4-diamino-butane, 1,6-diamino hexane, 1,8-diamino octane, Jeffamine ED-600.

Preferably, in said aminopolycarboxylic compound the aminopolycarboxylic acids have the general formula:

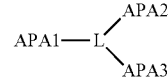

wherein APA1 is a hexadentate chelator, coupled via two amide functions onto solid phase and linker, APA2 and APA3 are hexadentate chelators, coupled to the linker via amide function, L is a linker molecule.

Preferably, in said aminopolycarboxylic compound the aminopolycarboxylic acids have the general formula:

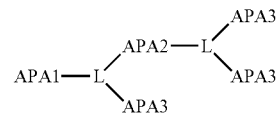

wherein APA1 is a hexadentate chelator, coupled via two amide functions onto solid phase and linker, APA2 is a hexadentate chelator, coupled via two amide functions onto linker, and APA3 are hexadentate chelators, coupled to the linker via amide function, L is a linker molecule.

Preferably, in said aminopolycarboxylic compound the linker molecule is a triamine.

Preferably, in said aminopolycarboxylic compound the linker molecule is selected from the group diethylene triamine, tris(2-aminoethyl)amine, tris(2-aminopropyl)amine, or amino-functionalized trifunctional branched PEGs, basing on a glycerol core.

Preferably, in said aminopolycarboxylic compound the aminopolycarboxylic acids have the general formula:

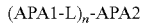

(APA1-L)$_n$-APA2 wherein the aminopolycarboxylic acids APA1 and APA2 are selected from EDTA, DTPA, TTHA, EDDS, EGTA, DOTA, and NOTA, which are coupled to the solid phase or linker via amide groups, and L is a bifunctional linker molecule;

Preferably, in said aminopolycarboxylic compound the aminopolycarboxylic acids have the general formula:

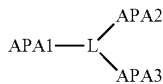

wherein APA1, APA2, and APA3 are selected from EDTA, DTPA, TTHA, EDDS, EGTA, DOTA, and NOTA, which are coupled to the solid phase or linker via amide groups, and L is a linker molecule.

Preferably, in said aminopolycarboxylic compound the polyamine is selected from the group diethylene triamine, triethylene tetramine, tetraethylene pentamine, pentaethylene hexamine, linear and branched polyethylene imine, poly-lysine, polypropylene imine, macrocylic polyamines like cyclam, cyclen, and 1,4,7-triazacyclononane, branched polyamines like 1,1,1-tris(aminomethyl)ethane, tris-aminoethyl amine, tris aminopropyl amine, tetrakis-ethylamino amine, tetrakis-ethylamino amine, tetrakis-aminopropyl amine, and amine functionalized tetrafunctional branched PEGs, basing on a pentaerithritol core.

Preferably, in said aminopolycarboxylic compound the polyamine is selected from the group triethylene tetramine, tetraethylene pentamine, pentaethylene hexamine.

Preferably, in said solid-phase immobilized aminopolycarboxylic acid compound the solid phase is selected from agarose, cellulose, agar, dextran, chitosan, alginate, gellan, more preferably agarose.

Preferably, in said solid-phase immobilized aminopolycarboxylic acid compound the solid phase is selected from silica, titanium dioxide, zirconium dioxide, aluminum dioxide, other metal- or semi-metal-oxides, gold, glass, or polymers from the group acrylates, methacrylates, acrylamides, styrene derivatives, vinyl esters, vinyl amides, or vinyl alcohol.

Preferably, in said solid-phase immobilized aminopolycarboxylic acid compound the solid phase is a porous or non-porous chromatographic support, a membrane, a coated surface, a coated tube, a sensor surface, a microarray surface, and a coated microtiter plate.

Preferably, in said solid-phase immobilized aminopolycarboxylic acid compound the solid phase is magnetic agarose, magnetic silica or a magnetic polymer, preferably magnetic agarose.

Preferably, in said solid-phase immobilized aminopolycarboxylic acid compound the aminopolycarboxylic acid is contacted with metal ions, selected from $Ni^{2+}$, $Co^{2+}$, $Cu^{2+}$, $Zn^{2+}$, $Al^{3+}$, $Fe^{3+}$, $Eu^{3+}$, $Ga^{3+}$, $Mn^{2+}$, $Ca^{2+}$;

According to a further aspect of the invention, the synthesis of said solid-phase immobilized aminopolycarboxylic acid compound consisting of a solid phase, spacer molecules, polyamines bound to the spacer molecule, and a plurality of aminopolycarboxylic acids covalently coupled to the polyamines, comprises the following steps:
a) providing EDTA and a solid phase comprising polyamine molecules;
b) coupling EDTA with the solid phase in the presence of a condensing agent, wherein a single group of EDTA reacts with the solid phase;
c) providing the solid-phase immobilized EDTA from step b) and a difunctional linker;
d) coupling the linker with an EDTA carboxy group in the presence of a condensing agent, wherein a single group of the linker reacts with EDTA;
e) providing the solid-phase immobilized EDTA with a linker covalently attached, from step d), and a second EDTA molecule;
f) coupling the second EDTA with the linker in the presence of a condensing agent, wherein a single group of the second EDTA reacts with the solid phase;
g) optionally repeating step c) to f) at least one time;
h) immobilizing metal ions by contacting the solid-phase immobilized aminopolycarboxylic acid compound with solutions of metal ions, selected from $Ni^{2+}$, $Co^{2+}$, $Cu^{2+}$, $Zn^{2+}$, $Al^{3+}$, $Fe^{3+}$, $Eu^{3+}$, $Ga^{3+}$, $Mn^{2+}$, $Ca^{2+}$.

According to a further aspect of the invention, the synthesis of said solid-phase immobilized aminopolycarboxylic acid compound consisting of a solid phase, spacer molecules, polyamines bound to the spacer molecule, and a plurality of aminopolycarboxylic acids covalently coupled to the polyamines, comprises the following steps:
a) providing EDTA dianhydride and a solid phase comprising polyamine molecules;
b) coupling said dianhydride to said carrier via amine group onto the solid phase, wherein a single anhydride group per EDTA reacts with an amine moiety and the other anhydride group remains unchanged;
c) washing the solid phase with an anhydrous solvent in order to remove the non-coupled dianhydride;
d) providing a solid-phase immobilized EDTA compound from step c) and a difunctional linker molecule;
e) coupling the linker with the EDTA anhydride group, wherein a single amine group of the linker reacts with the EDTA anhydride and the other functional group remains unchanged;
f) washing the solid phase with an anhydrous solvent in order to remove the non-coupled linker molecules;
g) providing the solid-phase immobilized EDTA with a linker covalently attached, from step f) and additional EDTA dianhydride;
h) coupling said dianhydride to said linker, wherein a single carboxy group per aminopolycarboxylic acid reacts with the amine moiety;
i) optionally repeating step c) to h) at least one time;
j) immobilizing metal ions by contacting the solid-phase immobilized aminopolycarboxylic acid compound with solutions of metal ions, selected from $Ni^{2+}$, $Co^{2+}$, $Cu^{2+}$, $Zn^{2+}$, $Al^{3+}$, $Fe^{3+}$, $Eu^{3+}$, $Ga^{3++}$, $Mn^{2+}$, $Ca^{2+}$.

According to a further aspect of the invention the synthesis of said solid-phase immobilized aminopolycarboxylic acid compound consisting of a solid phase, spacer molecules, polyamines bound to the spacer molecule, and a plurality of aminopolycarboxylic acids covalently coupled to the polyamines, comprises the following steps:
  a) providing EDTA dianhydride and a difunctional linker in a ratio of 2:1 to 1:1, preferably 2:1 to 1.25 to 1;
  b) coupling said dianhydride to said carrier via amine or hydroxy group onto the linker, wherein the linker reacts with two different dianhydrides, so that a substance APA1-L-(APA2-L) n-APA3 is formed, wherein APA1 is EDTA with one anhydride group and one amide function, APA2 is EDTA with two amide functions, and APA3 is EDTA with one anhydride group, n is 0 to 50, preferably 0 to 10;
  c) providing a solid phase comprising polyamine groups;
  d) coupling said linker-connected dianhydride to said carrier via amine group onto the solid phase, wherein a single carboxy group per aminopolycarboxylic acid reacts with the amine moiety and the other anhydride group remains unchanged;
  e) providing water or an aqueous puffer to hydrolyze the remaining anhydride groups;
  f) immobilizing metal ions by contacting the solid-phase immobilized aminopolycarboxylic acid compound with solutions of metal ions, selected from $Ni^{2+}$, $Co^{2+}$, $Cu^{2+}$, $Zn^{2+}$, $Al^{3+}$, $Fe^{3+}$, $Eu^{3+}$, $Ga^{3++}$, $Mn^{2+}$, $Ca^{2+}$;

According to a further aspect of the invention the synthesis of said solid-phase immobilized aminopolycarboxylic acid compound consisting of solid phase, spacer molecules, polyamines bound to the spacer molecule, and a plurality of aminopolycarboxylic acids covalently coupled to the polyamines, comprises the following steps:
  a) providing EDTA dianhydride and a trifunctional linker in a ratio of 3:1 to 9:4, preferably 3:1 to 5:2;
  b) coupling said dianhydride to said carrier via amine group onto the linker, wherein the linker reacts with three different dianhydrides, so that a reaction product of one of the following formulas is formed,

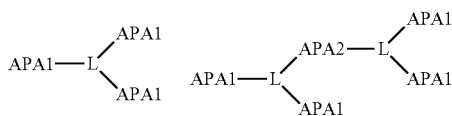

c) wherein APA1 is EDTA with one anhydride group and one amide group, APA2 is EDTA with two amide groups;
  d) providing a solid phase comprising polyamine groups;
  e) coupling said linker-connected EDTA to said carrier via amide group onto the polyamine-modified solid phase, wherein a single carboxy group per aminopolycarboxylic acid reacts with the amine moiety and the other anhydride groups remain unchanged;
  f) providing water or an aqueous puffer to hydrolyze the remaining anhydride groups;
  g) immobilizing metal ions by contacting the solid-phase immobilized aminopolycarboxylic acid compound with solutions of metal ions, selected from $Ni^{2+}$, $Co^{2+}$, $Cu^{2+}$, $Zn^{2+}$, $Al^{3+}$, $Fe^{3+}$, $Eu^{3+}$, $Ga^{3++}$, $Mn^{2+}$, $Ca^{2+}$.

Preferably, in the synthesis of said solid-phase immobilized aminopolycarboxylic acid compound the aminopolycarboxylic acids APA1, APA2, and APA3 are selected from EDTA, DTPA, TTHA, EDDS, EGTA, DOTA, and NOTA, which are coupled to the solid phase or linker via amide groups.

Preferably, in the synthesis of said solid-phase immobilized aminopolycarboxylic acid the bifunctional linker is a bifunctional molecule with one of the following formulas:

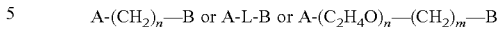

wherein A and B are functional groups, which are able to react with carboxylate groups and are selected from —$NH_2$, NHR, m and n are 2-20, L is a straight or branched configuration of 2-100 atoms, which can contain C, H, N, O and S, including cyclic compounds, such as carbon hydrates.

Preferably, in the synthesis of said solid-phase immobilized aminopolycarboxylic acid compound the bifunctional linker molecule is selected from the group ethylene diamine, 1,4-diamino-butane, 1,6-diamino hexane, 1,8-diamino octane, Jeffamine ED-600.

Preferably, in the synthesis of said solid-phase immobilized aminopolycarboxylic acid compound the trifunctional linker molecule is selected from the group diethylene triamine, tris(2-aminoethyl)amine, tris(2-aminopropyl)amine, or amino-functionalized trifunctional branched PEGs, basing on a glycerol core.

According to a further aspect the invention relates to the use of said solid-phase immobilized aminopolycarboxylic acid compounds in the field of molecular biology.

According to a further aspect the invention relates to the use of said solid-phase immobilized aminopolycarboxylic acid compound for the purification of proteins with a plurality of histidine residues.

According to a further aspect the invention relates to the use of said solid-phase immobilized aminopolycarboxylic acid compound for the purification of membrane proteins with a plurality of histidine residues.

According to a further aspect the invention relates to the use of said solid-phase immobilized aminopolycarboxylic acid compound for the purification of GPCRs with a plurality of histidine residues.

According to a further aspect the invention relates to the use of said solid-phase immobilized aminopolycarboxylic acid compound for the purification of transporter proteins with a plurality of histidine residues.

According to a further aspect the invention relates to the use of said solid-phase immobilized aminopolycarboxylic acid compound for the purification of proteins for therapeutical uses.

According to a further aspect the present invention relates to a method of purifying a recombinant protein or polypeptide, comprising the steps of:
  a) providing a solid-phase immobilized aminopolycarboxylic acid of any of the preceding claims, which has been loaded with metal ions, selected from $Ni^{2+}$, $Co^{2+}$, $Cu^{2+}$, $Zn^{2+}$, $Al^{3+}$, $Fe^{3+}$, $Eu^{3+}$, $Ga^{3++}$, $Mn^{2+}$,
  b) providing a sample containing a protein or polypeptide with a plurality of histidine moieties,
  c) contacting the sample with the solid-phase immobilized aminopolycarboxylic acid,
  d) separating the bound polypeptide or protein from the solution,
  e) eluting the recombinant protein or polypeptide form the solid phase;

Preferably, in the above method the protein is a membrane protein.

Preferably, in the above method the protein is a GPCR.
Preferably, in the above method the protein is an antigen.
Preferably, in the above method EDTA and imidazole can be added to the binding buffer in a concentration of at least 20 mM, and DTT can be added in a concentration of at least 10 mM, without interfering the metal binding and the protein yield.

According to a further aspect, the invention relates to the use of a metal-loaded solid-phase immobilized aminopolycarboxylic acid as defined further above for immobilized metal affinity chromatography (IMAC) in the purification of recombinant proteins or polypeptides with a plurality of histidine moieties.

According to a further aspect, the invention relates to the use of the solid-phase immobilized aminopolycarboxylic acid compound as defined further above for the purification of phosphoproteins.

According to a further aspect, the invention relates to the use of the solid-phase immobilized aminopolycarboxylic acid compound as defined further above for the purification of metalloproteins.

According to a further aspect, the invention relates to the use of the solid-phase immobilized aminopolycarboxylic acid compound as defined further above for the purification of nucleic acids.

Preferably, in the method of purifying a biomolecule as defined further above the solid-phase immobilized aminopolycarboxylic acid compound as defined further above can be washed with a sodium hydroxide solution in order to remove contaminants and sticking proteins to regenerate the material for further biomolecule purification and still has a protein binding capacity of at least 50 mg per ml.

In the following preferred embodiments of the invention will be described. Examples 1 to 6 comprise complete synthesis instructions for producing preferred solid-phase chelator materials. Comparative Example relates to the synthesis of a chelator material of the prior art. Furthermore the metal loading of the resins and the purification of 6×his-GFP with aminopolycarboxylic acid resins after sodium hydroxide treatment are described.

EXAMPLES

Examples for the Synthesis of the Solid-Phase Bound Chelator Chains

Example 1: Synthesis of a New Chelator by Preparation of Diethylene Triamine Agarose, Reaction of EDTA with Ethylene Diamine, and Covalent Coupling of EDTA-EDA-EDTA onto Agarose Synthesis of Diethylene Triamine Agarose 10 ml agarose particles (WorkBeads 40 SEC, BioWorks Sweden AB, Uppsala) are resuspended in 10 ml 1M caustic soda solution and incubated on a thermoshaker for two hours. Then 5 ml epichlorohydrine are added and the suspension is heated at 30° C. for four hours. The suspension is filtered via suction filtration and washed six times with dd water. Then the agarose is resuspended in 20 ml of a 5% diethylene triamine solution, pH 10.5, and incubated for twenty hours at 65° C. The agarose is suction-dried, washed four times with dd water, four times with phosphate-buffered saline and stored in anhydrous dimethylformamide.

Synthesis of EDTA-EDA-EDTA 853 mg EDTA dianhydride (3.33 mmol) are dissolved in 15 ml dimethylformamide and a solution of 100 mg ethylene diamine (1.67 mmol) in 5 ml dimethylformamide are added in short portions with intensive mixing. The reaction mixture is stirred for one hour at ambient temperature and for four hours at 60° C. The resulting product can be added directly to agarose without further purification.

Coupling onto Triamine Agarose 10 ml triamine agarose are resuspended in 10 ml dimethylformamide, and a solution of 600 mg EDTA-EDA-EDTA in 10 ml dimethylformamide is added. The reaction mixture is incubated for six hours at 60° C. and suction dried. After filtration, the product is washed six times with dimethylformamide.

Example 2: Synthesis of a New Chelator by Preparation of Pentaethylene Hexamine Agarose, Reaction of EDTA with Ethylene Diamine, and Covalent Coupling of EDTA-EDA-EDTA onto Agarose Synthesis of Pentaethylene Hexamine Agarose 10 ml agarose particles (WorkBeads 40 SEC, BioWorks Sweden AB, Uppsala) are resuspended in 10 ml 1M caustic soda solution and incubated on a thermoshaker for two hours. Then 5 ml epichlorohydrine are added and the suspension is heated at 30° C. for four hours. The suspension is filtered via suction filtration and washed six times with dd water. Then the agarose is resuspended in 20 ml of a 5%-pentaethylene hexamine solution, pH 10.5, and incubated for twenty hours at 65° C. The agarose is suction-dried, washed four times with dd water, four times with phosphate-buffered saline and stored in anhydrous dimethylformamide.

Synthesis of EDTA-EDA-EDTA 853 mg EDTA dianhydride (3.33 mmol) are dissolved in 15 ml dimethylformamide and a solution of 100 mg ethylene diamine (1.67 mmol) in 5 ml dimethylformamide are added in short portions with intensive mixing. The reaction mixture is stirred for one hour at ambient temperature and for four hours at 60° C. The resulting product can be added directly to agarose without further purification.

Coupling onto Hexamine Agarose.

10 ml hexamine agarose are resuspended in 10 ml dimethylformamide, and a solution of 600 mg EDTA-EDA-EDTA in 10 ml dimethylformamide is added. The reaction mixture is incubated for six hours at 60° C. and suction dried. After filtration, the product is washed six times with dimethylformamide.

Example 3: Formation of Dimeric EDTA Chains by Sequential Coupling of EDTA, Ethylene Diamine and EDTA Synthesis of Diethylene Triamine Agarose 10 ml agarose particles (WorkBeads 40 SEC, BioWorks Sweden AB, Uppsala) are resuspended in 10 ml 1M caustic soda solution and incubated on a thermoshaker for two hours. Then 5 ml epichlorohydrine are added and the suspension is heated at 30° C. for four hours. The suspension is filtered via suction filtration and washed six times with dd water. Then the agarose is resuspended in 20 ml of a 5% N-diethylene triamine solution, pH 10.5, and incubated for twenty hours at 65° C. The agarose is suction-dried, washed four times with dd water, four times with phosphate-buffered saline and stored in anhydrous dimethylformamide.

Synthesis of EDTA-Agarose (NH$_2$)

10 ml amino agarose are resuspended in 10 ml dimethylformamide, and a solution of 1500 mg 4,4'-Ethylenebis (2,6-morpholinedione) in 10 ml dimethylformamide are added. The reaction mixture is incubated for six hours at 60° C. and suction dried. After filtration, the product is washed six times with dry dimethylformamide.

Modification of EDTA Agarose with Ethylenediamine 10 ml of EDTA agarose are resuspended in 10 ml dimethylformamide, and a solution of 2 ml ethylene diamine in 10 ml dimethylformamide is added. After efficient mixing on a thermoshaker the suspension is allowed to react six hours at 65° C. Then the reaction product is suction-filtered, washed six times with dry dimethylformamide, and resuspended in dimethylformamide.
Reaction with EDTA Anhydride
10 ml of EDTA-EDA agarose are resuspended in 10 ml dimethylformamide, and a solution of 500 mg 4,4'-Ethylenebis(2,6-morpholinedione in 10 ml dimethylformamide is added. The reaction mixture is incubated for six hours at 60° C. and suction dried. After filtration, the product is washed three times with dimethylformamide, three times with dd water, three times with phosphate-buffered saline, and again once with dd water.

Example 4: Formation of Dimeric EDTA Chains by Synthesis of Jeffamine-Bridged EDTA, and Coupling onto Solid Phase Synthesis of EDTA-Jeffamine-EDTA 853 mg EDTA dianhydride (3.33 mmol) are dissolved in 15 ml dimethylformamide and a solution of 1000 mg Jeffamine-ED 600 (O,O-Bis(2-aminopropyl) polypropylene glycol-block-polyethylene glycol-block-polypropylene glycol, 1.67 mmol) in 10 ml dimethylformamide are added in short portions with intensive mixing. The reaction mixture is stirred for one hour at ambient temperature and for four hours at 60° C. The resulting product can be added directly to agarose without further purification.
Coupling onto Amine Agarose.
10 ml amino triamine agarose (example 1) are resuspended in 10 ml dimethylformamide, and a solution of 600 mg EDTA-EDA-EDTA in 10 ml dimethylformamide is added. The reaction mixture is incubated for six hours at 60° C. and suction dried. After filtration, the product is washed six times with dimethylformamide.

Example 5: Formation of Trimeric EDTA Chains by Synthesis of Ethylene Diamine-Bridged EDTA, and Coupling onto Solid Phase Synthesis of EDTA-EDA-EDTA-EDA-EDTA 853 mg EDTA dianhydride (3.33 mmol) are dissolved in 15 ml dimethylformamide and a solution of 133 mg ethylene diamine (2.22 mmol) in 5 ml dimethylformamide are added in short portions with intensive mixing. The reaction mixture is stirred for one hour at ambient temperature and for four hours at 60° C. The resulting product can be added directly to agarose without further purification. Coupling onto amine agarose.

10 ml triamine agarose (example 1) are resuspended in 10 ml dimethylformamide, and a solution of 600 mg EDTA-EDA-EDTA-EDA-EDTA in 10 ml dimethylformamide is added. The reaction mixture is incubated for six hours at 60° C. and suction dried. After filtration, the product is washed six times with dimethylformamide.

Example 6: Formation of Dimeric DTPA Chains by Sequential Coupling of DTPA, Ethylene Diamine and DTPA Synthesis of DTPA-Agarose 10 ml triamine agarose (example 1) are resuspended in 10 ml dimethylformamide, and a solution of 1500 mg DTPA dianhydride in 15 ml dimethylformamide is added. The reaction mixture is incubated for six hours at 60° C. and suction dried. After filtration, the product is washed six times with dimethylformamide.
Modification of DTPA Agarose with Ethylenediamine
10 ml of DTPA agarose are resuspended in 10 ml dimethylformamide, and a solution of 2 ml ethylene diamine in 10 ml dimethylformamide is added. After efficient mixing, the suspension is allowed to react six hours at 65° C. on a thermoshaker. Then the reaction product is suction-filtered, washed six times with dimethylformamide, and resuspended in dimethylformamide.
Reaction with DTPA Anhydride
10 ml of DTPA-EDA agarose are resuspended in 10 ml dimethylformamide, and a solution of 500 mg DTPA dianhydride in 10 ml dimethylformamide is added. The reaction mixture is incubated for six hours at 60° C. and suction dried. After filtration, the product is washed three times with dimethylformamide, three times with dd water, three times with phosphate-buffered saline, and again once with dd water.

Comparative Example 1: Synthesis of a New Chelator by Preparation of Amino Agarose, Reaction of EDTA with Ammonia, and Covalent Coupling of EDTA-EDA-EDTA onto Agarose Synthesis of Amino Agarose 10 ml agarose particles (WorkBeads 40 SEC, BioWorks Sweden AB, Uppsala) are resuspended in 10 ml 1M caustic soda solution and incubated on a thermoshaker for two hours. Then 5 ml epichlorohydrine are added and the suspension is heated at 30° C. for four hours. The suspension is filtered via suction filtration and washed six times with dd water. Then the agarose is resuspended in 20 ml of a 5% ammonia solution, pH 10.5, and incubated for twenty hours at 65° C. The agarose is suction-dried, washed four times with dd water, four times with phosphate-buffered saline and stored in anhydrous dimethylformamide.

Synthesis of EDTA-EDA-EDTA 853 mg EDTA dianhydride (3.33 mmol) are dissolved in 15 ml dimethylformamide and a solution of 100 mg ethylene diamine (1.67 mmol) in 5 ml dimethylformamide are added in short portions with intensive mixing. The reaction mixture is stirred for one hour at ambient temperature and for four hours at 60° C. The resulting product can be added directly to agarose without further purification. Coupling onto amino agarose.

10 ml amino agarose are resuspended in 10 ml dimethylformamide, and a solution of 600 mg EDTA-EDA-EDTA in 10 ml dimethylformamide is added. The reaction mixture is incubated for six hours at 60° C. and suction dried. After filtration, the product is washed six times with dimethylformamide.

Metal Loading of the Resins 10 ml of the chelating resin are suction-dried and washed three times with 0.1 M acetate, pH 6.0, and once with dd water. The residue is added to a 3% solution of nickel sulfate and incubated for three hours with stirring. Then the mixture is suction-dried, washed five times with dd water and can be stored in a low salt buffer, pH 6.0 to 7.0 in 30% ethanol to prevent microbial growth.

Alternatively, the resin may be loaded with cobalt, iron, aluminum, zinc, copper, and other transition metals or lanthanides by simply exchanging nickel sulfate against cobalt sulfate, iron sulfate, aluminum chloride, zinc chloride, copper sulfate, europium sulfate, and the like.

Purification of 6×his-GFP with Aminopolycarboxylic Acid Resins after Sodium Hydroxide Treatment 100 µl of the resin as 50% slurry were given in a column, and the supernatant was removed. Then every sample was washed two times with 4 ml 0.5 M sodium hydroxide, and after 5 minutes incubation the supernatants were removed.

Every column was washed two times with 4 ml binding buffer NPI-10 (50 mM $NaH_2PO_4$, 300 mM NaCl, 10 mM imidazole, pH 7.4) and incubated for 5 minutes.

10 mg of his-tagged GFP (green fluorescent protein) is added to lysis buffer NPI-10 (50 mM $NaH_2PO_4$, 300 mM NaCl, 10 mM imidazole, 10 mM EDTA, 10 mM DTT, pH 7.4) and incubated for 30 min with 100 µl of the resin as a 50% slurry.

After incubation the resin was washed two times with 2.5 ml NPI-20 (50 mM $NaH_2PO_4$, 300 mM NaCl, 20 mM imidazole, pH 7.4) and eluted three times with 1 ml NPI-250 (50 mM $NaH_2PO_4$, 300 mM NaCl, 250 mM imidazole, pH 8.0). The eluate fractions were combined, measured with 488 nm and the yields were calculated and summarized in Table 1. Gel picture of the eluates are shown in FIG. 1. The chelating additives (20 mM EDTA and 10 mM DTT) were added to NPI-10 to demonstrate the resistance of the tested resin to chelating agents, reductants and alkaline solutions.

TABLE 1

Results of protein purification

| Material | Protein binding capacity |
|---|---|
| Example 1 | 58 mg/ml |
| Comparative Example 1 | 17 mg/ml |

Result

The binding capacity of the material according to this invention is more than three times higher than the binding capacity of the material from the comparative example. It could be shown, that the chelating agent EDTA and the reductant DTT have no influence on the high capacity of the material according to this invention, and that the resin still shows a high protein binding capacity even after treatment with 0.5 M sodium hydroxide solution.

Example 7: Synthesis of a New Chelator by Preparation of Pentaethylene Hexamine Agarose, Reaction of EDTA with Ethylene Diamine, and Covalent Coupling of EDTA-EDA-EDTA onto Dextran Chips Synthesis of a Pentaethylene hexamine Dextran Chip A chip, basing on dextran-modified gold (SCR D200M-5, Xantec Bioanalytics GmbH, Dusseldorf, Germany) is resuspended in 10 ml 0.5M caustic soda solution and incubated on a thermoshaker for two hours. Then 5 ml epichlorohydrine are added and the suspension is heated at 30° C. for four hours. The supernatant is removed by decanting and the sample is washed six times with dd water. Then the chip is resuspended in 20 ml of a 5%-pentaethylene hexamine solution, pH 10.5, and incubated for twenty hours at 45° C. The supernatant is removed by decanting, washed four times with dd water, four times with phosphate-buffered saline and stored in anhydrous dimethylformamide.

Synthesis of EDTA-EDA-EDTA Chelator 853 mg EDTA dianhydride (3.33 mmol) are dissolved in 15 ml dimethylformamide and a solution of 100 mg ethylene diamine (1.67 mmol) in 5 ml dimethylformamide are added in short portions with intensive mixing. The reaction mixture is stirred for one hour at ambient temperature and for four hours at 60° C. The resulting product can be added directly to solid phases, fore example dextran chips, without further purification.

Chelator Coupling onto Hexamine Dextran Chip

The hexamine modified chip is resuspended in 10 ml dimethylformamide, and a solution of 600 mg EDTA-EDA-EDTA in 10 ml dimethylformamide is added. The reaction mixture is incubated for six hours at 60° C. and the supernatant removed by decanting. After filtration, the product is washed six times with dimethylformamide, four times with dd water, and three times with phosphate buffered saline.

Metal Loading

The chip is incubated in 2% nickel sulfate solution and incubated on a thermoshaker for two hours. Then the supernatant is removed by decanting, and the chip washed six times with dd water, three times with 20 mM acetate buffer, pH 6.0, and stored in 10 mM acetate, pH 6.5, 20% ethanol.

Example 8: Synthesis of Magnetic Particles with a New Chelator by Preparation of Pentaethylene Hexamine Agarose, Reaction of EDTA with Ethylene Diamine, and Covalent Coupling of EDTA-EDA-EDTA onto Magnetic Agarose Synthesis of Pentaethylene Hexamine Magnetic Beads 10 ml magnetic agarose particles (Cube Biotech, Monheim, Germany) are resuspended in 10 ml 1M caustic soda solution and incubated on a thermoshaker for two hours. Then 5 ml epichlorohydrine are added and the suspension is heated at 30° C. for four hours. The supernatant is removed by magnetic separation and the magnetic beads washed six times with dd water. Then the magnetic agarose is resuspended in 20 ml of a 5%-pentaethylene hexamine solution, pH 10.5, and incubated for twenty hours at 65° C. The supernatant is removed by magnetic separation and the magnetic beads washed four times with dd water, four times with phosphate-buffered saline and stored in anhydrous dimethylformamide.

Synthesis of EDTA-EDA-EDTA Chelator 853 mg EDTA dianhydride (3.33 mmol) are dissolved in 15 ml anhydrous dimethylformamide and a solution of 100 mg ethylene diamine (1.67 mmol) in 5 ml dimethylformamide is added in short portions with intensive mixing. The reaction mixture is stirred for one hour at ambient temperature and for four hours at 60° C. The resulting product can be added directly to magnetic agarose without further purification.

Chelator Coupling onto Hexamine Magnetic Agarose 10 ml hexamine magnetic beads are resuspended in 10 ml dimethylformamide, and a solution of 600 mg EDTA-EDA-EDTA in 10 ml dimethylformamide is added. The reaction mixture is incubated for six hours at 60° C. and the supernatant removed by magnetic separation. Then the product is washed six times with dimethylformamide, and four times with dd water.

Metal Loading 10 ml chelator-functionalized magnetic beads are resuspended in 20 ml 2% nickel sulfate solution and incubated on a thermoshaker for two hours. Then the supernatant is removed by magnetic separation, and the chip washed six times with dd water, three times with 20 mM acetate buffer, pH 6.0, and stored in 10 mM acetate, pH 6.5, 20% ethanol.

Example 9: Synthesis of a Membrane Coated with a New Chelator by Preparation of Pentaethylene Hexamine Agarose, Reaction of EDTA with Ethylene Diamine, and Covalent Coupling of EDTA-EDA-EDTA onto Magnetic Agarose CIM Epoxy columns (Bia Separations, Ajdovščina, Slovenia) are purged for ten minutes with dd water by means of a peristaltic pump. Then a solution of 20 ml in 80 ml 1M NaOH is heated to 35° C. and purged through the columns for three hours.

After that the columns are washed with dd water for twenty minutes, and a solution of 5% pentaethylene hexamine in dd water, pH 10.5, is purged through the column at 60° C. for ten hours.

After a dd water wash in 20 minutes and a DMF wash in 10 minutes, an EDTA-EDA-EDTA solution (prepared after description above) is pumped through the column at 50° C. for eight hours. In the next steps, dd water, phosphate buffer, pH 7.0, and dd water are pumped through the column, each ten minutes.

Then the column is incubated in a 1% nickel sulfate solution for one hour, and dd water wash is repeated for twenty minutes. The protein binding capacity of this column is 2-5 mg, determined with his-GFP, and this column is stable against alkaline solutions and EDTA.

Example 10: Synthesis of a Surface Coated with a New Chelator by Preparation of Pentaethylene Hexamine Agarose, Reaction of EDTA with Ethylene Diamine, and Covalent Coupling of EDTA-EDA-EDTA onto Magnetic Agarose 8-well strips, activated with maleic anhydride, basing on dextran-modified gold (SCR Pierce™ Maleic Anhydride Activated Plates, Clear, 8-Well Strip, catalogue No. 15100, Pierce, Rockford, USA) are washed with 200 µl each. Then 100 µl of a solution of 5% pentaethylene hexamine in dd water, pH 10.5, are added, and the plate is incubated at a shaker for three hours at 37° C.

The amine solution is removed, and the wells are washed six times with dd water, and four times with diethyl ether. Then a suspension of 5 mg EDTA-EDA-EDTA in 150 µl diethylether is added, and the plate shaken on a shaker at room temperature.

The plate is washed three times with dd water, three times with phosphate buffer, pH 7.0, and once with dd water. In the next step 125 µl of a 2% nickel sulfate solution is added, and the plate is shaken on a shaker for two hours at room temperature. After five washes with dd water, the plate can be used for protein purification.

Results

Affinity Measurement with Surface Plasmon Resonance

The chelator modified chip has been investigated with a 2SPR surface plasmon resonance system (Reichert, Buffalo, USA).

For this experiment the running buffer and blank buffer were 50 mM Hepes, 150 mM NaCl, 1 mM EDTA, pH 7.6, and the imidazol buffer 50 mM Hepes, 150 mM NaCl, 600 mM Imidazol, pH 7.6. The protein used was SMOX (62.64 kDa, N-term. His Tag), with a concentration fo 3 mg/ml.

With running buffer, the protein concentration was adjusted to 25 µM, 12.5 µM, 6.25 µM, 3.125 µM, 1.56 µM, 0.78 µM, 0.390 µM, and 0.195 µM.

The flow rate used was 15 µl/min, and the following solutions were applied:

Running buffer with protein for an association time of 8 minutes, then pure running buffer for a dissociation time of 20 minutes. Then imidazole buffer was applied for an association time of 4 minutes and a dissociation time of 2 minutes.

Curves showing signal intensity against time were recorded and plotted.

As a comparative example 2, NiHC 1000M Chips (Xantec Bioanalytics GmbH, Duesseldorf, Germany) were processed with the same protein and buffers.

The results show, that because of the low affinity, the protein starts dissociating from Ni-NTA chips during dissociation time with running buffer. The chelate-functionalized chips according to this patent application show a horizontal line, showing no significant loss of protein with running buffer, due to the higher affinity of the chelator.

What is claimed is:

1. A solid-phase chelator material comprising a solid phase, polyamine groups bound to the solid phase and chelating groups bound to the polyamine groups, wherein at least a part of the polyamine groups are connected with at least two chelating groups per polyamine group and wherein each chelating group comprises one or several aminopolycarboxylic acid groups (APA groups), with the proviso that the number of APA groups per polyamine group connected with at least two chelating groups is at least three, wherein the APA groups are derived from the APAs which are selected from the group consisting of ethylenediaminetetraacetic acid, diethylenetriaminepentaacetic acid, triethylenetetraminehexaacetic acid, ethylenediamine-N,N'-disuccinic acid, ethyleneglycol-bis(β-aminoethyl ether)-N,N,N',N'-tetraacetic acid, 1,4,7,10-tetraazacyclododecane-1,4,7,10-tetraacetic acid, and 1,4,7-triazacyclononane-1,4,7-trisacetic acid, and wherein the polyamine groups are derived from the polyamines which are selected from the group consisting of diethylene triamine, triethylene tetramine, tetraethylene pentamine, penta ethylene hexamine, linear and branched polyethylene imine, poly-lysine, polypropylene imine, macrocylic polyamines cyclam and cyclen, the branched polyamines 1,1,1-tris(aminomethyl)ethane, tris-aminoethyl amine, tris aminopropyl amine, tetrakis-ethylamino amine.

2. The solid-phase chelator material according to claim 1, wherein the chelating groups are selected from the group consisting of individual APA groups, linear chelator chains formed by two or more APA groups which are connected with each other via bifunctional linker moieties K, branched chelator chains formed by three or more APA groups connected with each other via trifunctional linker moieties L, and mixed chelator chains formed by four or more APA groups connected with each other via at least one bifunctional linker moiety K and at least one trifunctional linker moiety L.

3. The solid-phase chelator material according to claim 2, wherein
the bifunctional linker moiety K is selected from the group consisting of A-$(CH_2)_n$—B, A-Q-B and A-$(C_2H_4O)_m$—$(CH_2)_o$—B, in which A and B are functional groups which are able react with carboxy groups, namely OH, $NH_2$, NHR, Cl, Br, I, OMs, OTs, $N_3$, wherein R is a hydrocarbon group with the formula $C_nH_{2n+1}$, in which n is an integer in the range from 1 to 6, m is an integer in the range from 1 to 12, o is an integer in the range from 2 to 12, Q is a straight or branched configuration of 2 to 100 atoms; and
the trifunctional linker moiety L has one of the general formulas

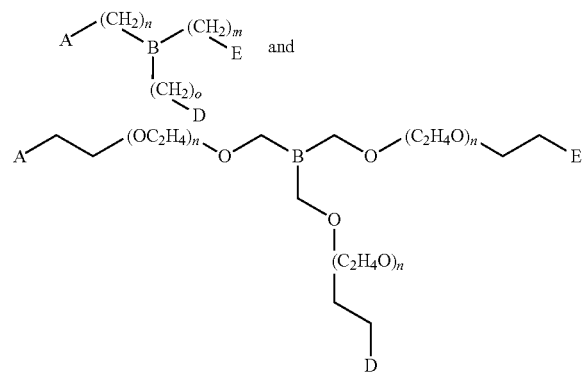

in which A, D and E are functional groups which are able to react with a carboxy group, namely —$NH_2$ or —NHR, B is a branching atom, namely C or N, which is connected with at least three stable bonds to carbon atoms, connected with functional groups, and n, m and o are integers in the range from 2 to 30.

4. The solid-phase chelator material according to claim 1, wherein the number of chelating groups bound to a polyamine group is at least four, and/or wherein the number of APAs which is coupled to a polyamine group connected with at least two chelating groups is in the range from 4 to 15.

5. The solid-phase chelator material according to claim 1, wherein at least a part or all of the chelating groups have the general formula -(APA1-K)$_n$-APA2 in which APA1 and APA2 are identical or different from each other, n is an integer in the range from 1 to 50 and K is a bifunctional linker moiety.

6. The solid-phase chelator material according to claim 1, wherein at least a part or all of the chelating groups

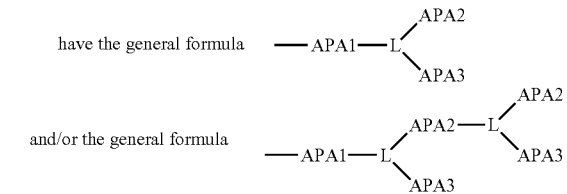

in which APA1, APA2 and APA3 are aminopolycarboxylic acid groups which are identical or different from each other and L is a trifunctional linker moiety.

7. The solid-phase chelator material according to claim 1, wherein the APAs and the linker moieties and/or the chelating groups and the polyamine groups are connected with each other via an amide moiety.

8. The solid-phase chelator material according to claim 1, wherein a spacer moiety is inserted between the solid phase and the polyamine groups which is derived from the group consisting of epichlorohydrine, epibromohydrine, 1,2-ethylene glycol diglycidyl ether, 1,4-butanediol diglycidyl ether, allyl glycidyl ether and allyl bromide.

9. The solid-phase chelator material according to claim 1, wherein the solid phase is selected from the group consisting of
agarose, cellulose, agar, dextran, chitosan, alginate, gellan, and/or
silica, titanium dioxide, zirconium dioxide, aluminum dioxide, other metal- or semi-metal-oxides, gold, glass, and/or
acrylates, methacrylates, acrylamides, styrene derivatives, vinyl esters, vinyl amides, and vinyl alcohol, and/or
porous chromatographic supports, non-porous chromatographic supports, membranes, coated surfaces, coated tubes, sensor surfaces, microarray surfaces, coated microtiter plates, and/or
magnetic agarose, magnetic silica and a magnetic polymer, and/or
dextran modified gold chips, magnetic beads.

10. A metal ion loaded solid-phase chelator material comprising a solid-phase chelator material according to claim 1 loaded with metal ions selected from the group consisting of $Ni^{2+}$, $Co^{2+}$, $Cu^{2+}$, $Zn^{2+}$, $Al^{3+}$, $Fe^{3+}$, $Eu^{3+}$, $Ga^{3+}$, $Mn^{2+}$, and $Ca^{2+}$.

11. A method for producing a solid-phase chelator material as claimed in claim 1, the method comprising
covalently binding at least three monomeric APAs on a solid phase having polyamine groups bound thereto under formation of polyamine groups having at least three monomeric APA groups bound thereto via an amide group, or
covalently binding at least two APAs on a solid phase having polyamine groups bound thereto under formation of a solid-phase material with polyamine groups having at least two APA groups bound thereto via an amide group, adding a bifunctional linker K or a trifunctional linker L to said solid-phase material, reacting said coupled linker with a carboxy group of a second APA, thereby forming a solid-phase chelator material having linear chelator chains or branched chelator chains of APA groups bound to the polyamine groups bound to the solid phase, optionally repeating the steps of adding a linker and then adding a further APA for extending the length of the linear chelator chains or the branched chelator chains; or reacting at least two monomeric APAs with a bifunctional linker K or at least three monomeric APAs with a trifunctional linker L under formation of a multimeric APA chelator comprising a linear chelator chain or a branched chelator chain and covalently binding at least two multimeric APA chelators on a solid phase having polyamine groups bound thereto under formation of polyamine groups having at least two linear and/or branched chelator chains bound thereto via an amide group.

12. A method for producing a solid-phase chelator material having linear chelating groups with APA groups connected via a bifunctional linker as claimed in claim 1, the method comprising the following steps:
   a) providing an APA and a solid phase having polyamine groups bound thereto;
   b) coupling the APA with the solid phase in the presence of a condensing agent, wherein a single carboxy group of the APA reacts with the solid phase under binding of the APA to the solid phase;
   c) mixing the solid-phase material obtained in step b) with a bifunctional linker K;
   d) coupling the bifunctional linker K with an APA carboxy group in the presence of a condensing agent, wherein a single reactive group of the bifunctional linker K reacts with the bound APA;
   e) mixing the solid-phase material obtained in step d) with a further APA;
   f) coupling the further APA with the bifunctional linker in the presence of a condensing agent, wherein a single carboxy group of the further APA reacts with a further reactive group of the bifunctional linker K bound to the solid-phase material;
   g) optionally repeating step c) to f) at least one time.

13. A method for producing a solid-phase chelator material having linear chelating groups with APA groups connected via a bifunctional linker as claimed in claim 1, the method comprising the following steps:
   a) providing an APA dianhydride and a solid-phase material having polyamine groups bound thereto;
   b) coupling said APA dianhydride with said solid-phase material via an amino group of bound polyamine, wherein a single anhydride group per APA dianhydride reacts with an amino moiety and the other anhydride group remains unchanged;
   c) washing the solid-phase material obtained in step b) with an anhydrous solvent in order to remove the non-coupled dianhydride;
   d) providing the solid-phase material obtained in step c) and a bifunctional linker K;
   e) coupling the bifunctional linker K with the APA anhydride group, wherein a single amine group of the bifunctional linker K reacts with the APA anhydride group and the other functional group of the bifunctional linker K remains unchanged;
   f) washing the solid phase with an anhydrous solvent in order to remove the non-coupled linker molecules;
   g) providing the solid-phase material obtained in step f) and additional APA dianhydride;
   h) coupling said APA dianhydride to said bifunctional linker K, wherein a single carboxy group per APA reacts with the remaining functional group of the bifunctional linker K;
   i) optionally repeating step c) to h) at least one time.

14. A method for producing a solid-phase chelator material having linear chelating groups with APA groups connected via a bifunctional linker as claimed in claim 1, the method comprising the following steps:
   a) providing an APA dianhydride and a bifunctional linker K in a ratio of 2:1 to 1:1;
   b) coupling the APA dianhydride to said bifunctional linker K via an amine or a hydroxy group on the linker, wherein the linker reacts with two different dianhydrides, so that a substance APA1-K-(APA2-K)$_n$-APA3 is formed, wherein APA1 is an APA with one anhydride group and one amide function, APA2 is an APA with two amide functions, and APA3 is an APA with one anhydride group, n is in the range from 0 to 50, and K is a bifunctional linker moiety;
   c) providing a solid phase having polyamine groups bound thereto;
   d) coupling said linker-connected dianhydride to said carrier via an amino group of a polyamine group bound to the solid phase, wherein a single carboxy group per APA reacts with the amine moiety and the other anhydride group remains unchanged;
   e) providing water or an aqueous puffer to hydrolyze the remaining anhydride groups.

15. A method for producing a solid-phase chelator material having branched chelating groups comprising APA groups connected via a trifunctional linker as claimed in claim 1, the method comprising the following steps:
   a) mixing an APA dianhydride and a trifunctional linker L in a ratio of 3:1 to 9:4, and a solid phase with bound polyamine groups;
   b) coupling the APA dianhydride to a solid-phase carrier via amine group onto the linker, wherein the linker reacts with three different dianhydrides, so that a reaction product of one of the following formulas is formed,

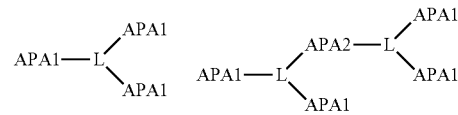

wherein APA1 is an APA group with one anhydride group and one amide group, APA2 is an APA with two amide groups and L is a trifunctional linker moiety;
   c) providing a solid phase comprising polyamine groups;
   d) coupling said linker-connected APA to said carrier via amide group onto the polyamine-modified solid phase, wherein a single carboxy group per aminopolycarboxylic acid reacts with the amine moiety and the other anhydride groups remain unchanged;
   e) providing water or an aqueous puffer to hydrolyze the remaining anhydride groups.

16. A method for producing a metal ion load solid-phase chelator material comprising carrying out the method according to claim 11 for producing a solid-phase chelator material and then immobilizing metal ions by contacting the solid-phase chelator material with a solution of metal ions which are selected from the group consisting of Ni$^{2+}$, Co$^{2+}$, Cu$^{2+}$, Zn$^{2+}$, Al$^{3+}$, Fe$^{3+}$, Eu$^{3+}$, Ga$^{3++}$, Mn$^{2+}$, Ca$^{2+}$.

17. A method for purifying a recombinant protein or polypeptide, comprising the steps of:
   a) providing a metal loaded solid-phase chelator material according to claim 10;

b) providing a sample containing the recombinant protein or polypeptide,
c) contacting the sample with the metal loaded solid-phase chelator material;
d) separating bound polypeptide or recombinant protein from the solution;
e) eluting the recombinant protein or polypeptide form the solid phase.

18. The method according to claim 17, wherein the recombinant protein is selected from the group consisting of membrane proteins, GPCRs and antigens.

19. The method according to claim 17, wherein EDTA and imidazole are added to a binding buffer in a concentration of at least 20 mM, and DTT (dithiothreitol) is added in a concentration of at least 10 mM, without interfering with metal binding and protein yield.

* * * * *